(12) United States Patent
Sload et al.

(10) Patent No.: US 12,404,199 B2
(45) Date of Patent: Sep. 2, 2025

(54) MODULAR ANAEROBIC DIGESTION POINT-OF-WASTE RENEWABLE ENERGY APPARATUS AND METHOD

(71) Applicant: ITility, L.L.C., Chantilly, VA (US)

(72) Inventors: Pete Sload, Washington, VA (US); Erik Overby, Purcellville, VA (US); Benjamin Frank, Germantown, MD (US); Kevin Lauer, Front Royal, VA (US); Eric Walberg, Brookfield, CT (US)

(73) Assignee: ITility, L.L.C., Chantilly, VA (US)

( * ) Notice: Subject to any disclaimer, the term of this patent is extended or adjusted under 35 U.S.C. 154(b) by 646 days.

(21) Appl. No.: 17/863,868

(22) Filed: Jul. 13, 2022

(65) Prior Publication Data
US 2023/0016345 A1     Jan. 19, 2023

Related U.S. Application Data

(60) Provisional application No. 63/221,328, filed on Jul. 13, 2021.

(51) Int. Cl.
*C02F 11/04* (2006.01)
*B01D 53/02* (2006.01)
(Continued)

(52) U.S. Cl.
CPC ............ *C02F 11/04* (2013.01); *B01D 53/02* (2013.01); *B01D 53/26* (2013.01); *C12M 21/04* (2013.01);
(Continued)

(58) Field of Classification Search
CPC .......... B01D 53/1468; B01D 2253/102; B01D 2257/304; B01D 2256/245; B01D 53/02;
(Continued)

(56) References Cited

U.S. PATENT DOCUMENTS 8,221,626 B2   7/2012  Sassow
8,465,645 B2   6/2013  Sassow
(Continued)

FOREIGN PATENT DOCUMENTS

WO   2013039407 A1   3/2013
WO   2016005770 A2   1/2016

OTHER PUBLICATIONS

SEab Power Ltd. t/a SeaB Energy, Muckbuster®, Jun. 29, 2021, London, England.

*Primary Examiner* — Claire A Norris
(74) *Attorney, Agent, or Firm* — Breiner & Breiner, L.L.C

(57) ABSTRACT

There is disclosed a modular anaerobic digestion point-of-waste to renewable energy system. The system is directed to a modular and scalable anaerobic digestion system for point-of-waste use. The System includes a pre-treatment process for removing inhibitory nutrients from a feedstock, an in-treatment process for providing clean renewable energy and a post-treatment process for further providing clean renewable energy for subsequent use. The System includes a leaching bed; a liquids tank; a mixing tank; an anaerobic digester reactor; a precipitation tank; a stripping tank; a hydrogen sulfide scrubber; a water remover; a gas bladder; a dewaterer; and a flare system.

12 Claims, 20 Drawing Sheets

(51) Int. Cl.
- *B01D 53/26* (2006.01)
- *C12M 1/00* (2006.01)
- *C12M 1/06* (2006.01)
- *C12M 1/107* (2006.01)
- *C12M 3/00* (2006.01)
- *C12P 5/02* (2006.01)
- C02F 101/10 (2006.01)
- C02F 101/16 (2006.01)

(52) U.S. Cl.
CPC ............ *C12M 23/44* (2013.01); *C12M 23/58* (2013.01); *C12M 27/02* (2013.01); *C12M 47/18* (2013.01); *C12P 5/023* (2013.01); *B01D 2253/102* (2013.01); *B01D 2257/304* (2013.01); *C02F 2101/105* (2013.01); *C02F 2101/16* (2013.01); *C02F 2201/007* (2013.01)

(58) Field of Classification Search
CPC .......... B01D 53/26; C02F 1/20; C02F 1/5236; C02F 1/66; C02F 11/04; C02F 11/125; C02F 2101/101; C02F 2101/105; C02F 2101/16; C02F 2103/20; C02F 2201/007; C02F 2209/02; C02F 2209/06; C02F 2301/046; C02F 9/00; C12M 21/04; C12M 23/36; C12M 23/44; C12M 23/58; C12M 27/02; C12M 29/18; C12M 47/18; C12P 5/023
USPC ........................................................ 210/603
See application file for complete search history.

(56) References Cited

U.S. PATENT DOCUMENTS

| | | |
|---|---|---|
| 9,272,930 B2 | 3/2016 | Sassow |
| 9,409,806 B2 | 8/2016 | Knoop |
| 9,682,880 B2 | 6/2017 | Sassow |
| 2004/0191755 A1 | 9/2004 | Kemper et al. |
| 2011/0200954 A1* | 8/2011 | Sassow ................... C05F 11/00 431/2 |
| 2012/0064562 A1 | 3/2012 | Allen et al. |
| 2014/0147911 A1 | 5/2014 | Allen et al. |
| 2016/0083683 A1 | 3/2016 | Augustine et al. |
| 2018/0030399 A1 | 2/2018 | Allen et al. |

\* cited by examiner

MODULAR ANAEROBIC DIGESTION POINT-OF-WASTE RENEWABLE ENERGY APPARATUS AND METHOD

RELATED APPLICATION

This application claims benefit of U.S. Provisional Application Ser. No. 63/221,328, filed Jul. 13, 2021, entitled "Modular Anaerobic Digestion Point-Of-Waste Renewable Energy Apparatus And Method," which application is incorporated herein by reference in its entirety.

FIELD OF THE INVENTION

The present invention relates to a modular anaerobic digestion point-of-waste to renewable energy system. More particularly, the invention relates to a modular and scalable anaerobic digestion system for point-of-waste use, including a pretreatment process for removing inhibitory nutrients from the feedstock, an in-treatment process for providing clean renewable energy and a post-treatment process for further providing clean renewable energy for subsequent use.

BACKGROUND OF THE INVENTION

Anaerobic digestion systems are known in the art. Similarly, mobile modular anaerobic digestion systems have been disclosed such as in WO2013/039407. However, such systems are not optimal in their use, including lacking the ability to: leach feedstocks such as chicken manure prior to anaerobic digestion thereby precluding effective digestion; remove phosphorus from the feedstocks; remove nitrogen from the feedstocks; and remove hydrogen sulfide from the biogas.

Much of the population pays to have their organic waste removed and taken to a waste treatment plant or reuses their waste as fertilizer, presenting potential issues regarding nutrient runoff into local watersheds. There is a need for an efficient mobile and modular system which can be scaled to a user's demands.

Additionally, present anaerobic digestion systems do not allow for modularity in the system, meaning that the capacity of the system is fixed, and offer no option for stripping environmentally harmful nutrients from the waste, rendering the digestate unusable as fertilizer in certain regions with restrictions on the release of such chemicals, e.g., Maryland, USA. The ability to sequester these nutrients from feedstocks is desirable, including the handling of a wide variety of feedstocks with potentially disparate nutrient contents, e.g., cow manure, chicken manure, and food waste.

These and other shortcomings of these known apparatus and methods are addressed by the present invention.

SUMMARY OF THE INVENTION

It is a primary object of the invention to provide a modular anaerobic digestion point-of-waste to renewable energy system ("System") providing for ease of transportation, deployment, construction, cost efficient, and sized for energy output. The System of components is designed as a "plug and play" System.

It is another primary object of the invention to provide a scalable system which may process any volume of waste by simply altering the component sizing.

It is another primary object of the invention to provide a point-of-waste System which will reduce transportation costs, thus reducing carbon footprint.

It is another primary object of the invention to provide a hybrid feedstock loading System, namely, batch, continuous flow, or a combination.

It is another primary object of the invention to provide a System for leaching and for nutrient recovery.

It is another primary object of the invention to provide a System for mixing feedstock in preparation for digestion.

It is another primary object of the invention to provide a System for stripping ammonia and/or hydrogen sulfide.

It is another primary object of the invention to provide a System for precipitating phosphorous for mitigation of runoff from digestate.

It is another primary object of the invention to provide a System for nutrient recovery which customizes nutrient content for use of solids or cake as fertilizer and provides for flexibility of product composition.

The System offers an effective waste management solution by converting organic material, feedstock, into biogas and digestate which can be separated into solid and liquid liquor components by dewatering. The System includes a leaching bed for feedstocks that require pre-treatment to reduce undesirable nutrients in the organic material prior to anaerobic digestion ("AD"). In a mixing tank, including a portable tank, organic material such as, but not limited to, animal manure and food waste, is (after leaching, if necessary) blended using a mixer with liquids, including water or liquor from a previous batch, to create a feedstock of the appropriate solids content required for AD. The exact dilution will depend upon the organic material processed. A water meter attached along a pipe leading from a liquids tank to the mixing tank measures the amount of liquid pumped into the mixing tank, allowing for accurate feedstock preparation. Once the material in the mixing tank has been blended thoroughly providing for a feedstock slurry, a pump transfers the feedstock slurry to an anaerobic digester reactor ("AD reactor"). There, anaerobic digestion initiates conversion of the organic material into biogas. During digestion, the feedstock slurry may be run through a precipitation tank and a stripping tank to capture ammonia and phosphorus to reduce the concentration of these compounds in the final digestate. Stripping of ammonia reduces the nitrogen content in certain feedstocks, e.g., chicken manure, and improves their digestion. The precipitation helps reduce the phosphorus in the resulting digestate, which is important for projects located in regions which restrict the release of phosphorus from fertilizers. The stripping system may also be used to remove sulfur and carbon dioxide from the feedstock slurry to improve conditions for microbes and offer options for additional nutrient capture. The produced biogas contains methane, carbon dioxide, and trace amounts of other components. As the gas is produced, it passes through a treatment system which dries it and removes hydrogen sulfide ($H_2S$) gas. The biogas treatment System may use a water remover tank comprising a refrigerated coiled tube or desiccant dryer which condense water from the biogas as it passes through, effectively removing it from the gaseous mixture. The gas may travel to an $H_2S$ scrubber featuring both an iron treatment scrubber and an activated charcoal treatment scrubber. The gas is then fed into a compressor that compresses the gas into a bladder or tank for storage. At this point, the methane within the evolved biogas can be used with any natural gas compatible appliance/generator, combined heat and power ("CHP") engine, or be routed from the bladder to a flare system. Importantly, the System may be scaled to handle any volume of waste by altering the size of the requisite components.

The invention is, therefore, directed to a modular anaerobic digestion point-of-waste to renewable energy system for converting an organic feedstock material into a biogas and a digestate which digestate is separated into solid and liquid components by dewatering. This apparatus and method comprises a leaching bed adapted to receive the organic feedstock material and water to remove inhibitory nutrients; a mixing tank adapted to receive from the leaching bed the leached feedstock; a liquids tank adapted to provide liquids to the mixing tank; a means for macerating the feedstock and the liquids in the mixing tank into a feedstock slurry; an anaerobic digester reactor wherein the feedstock slurry is pumped from the mixing tank into the anaerobic digester reactor and wherein anaerobic digestion takes place to convert the feedstock slurry into the biogas and the digestate; a precipitation tank and a stripping tank wherein a portion of the feedstock slurry in the anaerobic digestion reactor is pumped first into the precipitation tank and then into the stripping tank, the precipitation tank and the stripping tank are adapted to clean the feedstock slurry of at least ammonia and phosphorus, wherein the cleaned feedstock slurry is pumped back into the anaerobic digester reactor; a hydrogen sulfide scrubber adapted to receive the biogas wherein the hydrogen sulfide scrubber removes hydrogen sulfide from the biogas; a water remover tank adapted to receive the biogas wherein water is removed from the biogas; a gas bladder adapted to receive the biogas from the hydrogen sulfide scrubber wherein the biogas is stored for subsequent use; a dewaterer adapted to receive the digestate from the anaerobic digester reactor wherein the digestate is dewatered for subsequent use; and wherein the system is adapted to be located at the point-of-waste and is adapted to be scaled to handle the volume of organic material by alternating the size of the components thereof.

The implementation of the System provides for the sustainable production of biogas with the added benefit of NPK fertilizers and an end state cake that can also be used as a fertilizer without the negative impacts of nutrient runoff, e.g., phosphorus and nitrogen, into waterways. Furthermore, the isolation of potassium, phosphorus, and nitrogen in separate byproducts enables the ability to produce custom fertilizers through controlled recombination of these three vital crop nutrients. The System's modularity and flexibility allow for nearly any organic waste feedstock to be used in the System regardless of its source. A goal of the System is to reduce the user's dependency on utility providers, mitigate harmful runoff of nutrients, and reduce the user's carbon footprint.

These primary and other objects of the invention will be apparent from the following description of the preferred embodiments of the invention and from the accompanying drawings.

BRIEF DESCRIPTION OF THE DRAWINGS

The following detailed description of the specific non-limiting embodiments of the present invention can be best understood when read in conjunction with the following drawings, where like structures are indicated by like reference numbers.

Referring to the Drawings.

DETAILED DESCRIPTION OF THE INVENTION

The invention provides solutions to the limitations of the prior art as described above. The invention has built upon the advantages of the prior art with the advantage of enabling the user to customize the processed volume of the System as well as its feedstock treatment options. The System's modularity allows for multiple AD reactors to work in conjunction with one another to process any volume of waste produced by a user. Additionally, the components and operation of the System can be adjusted based on the requirements and composition of the feedstock in question.

Depending on the type of feedstock, the leaching bed, the precipitation tank and the stripping tank may or may not be necessary. The purpose of the precipitation and stripping process is to clean the feedstock of environmentally harmful nutrients such as nitrogen and phosphorus. This capability is particularly important when processing feedstocks high in these nutrients, e.g., chicken manure, or when operating in regions where the release of such chemicals are strictly regulated, e.g. Maryland, USA.

Figure 1A:
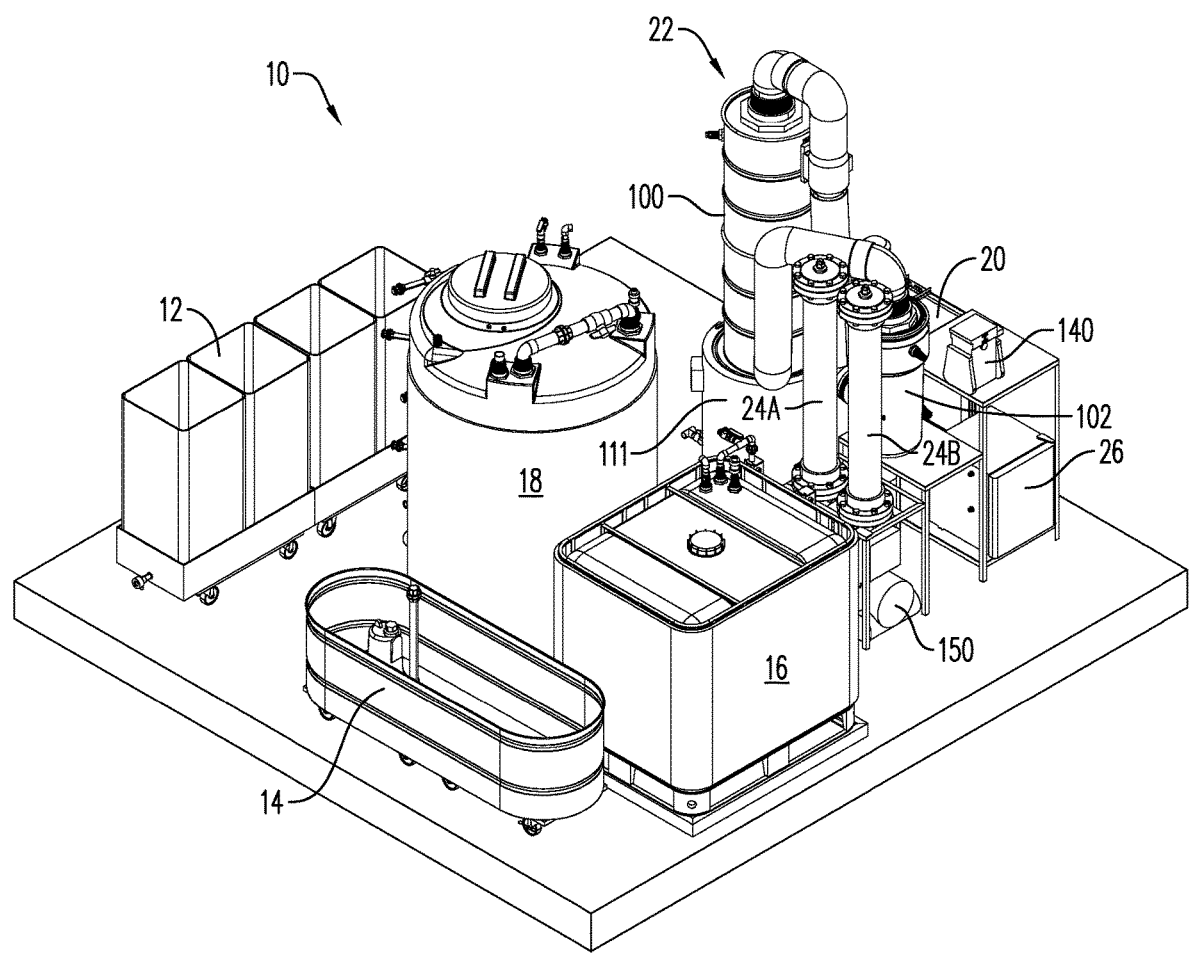
FIG. 1A is a plan view of the modular anaerobic digestion system of the invention.
Figure 1B:
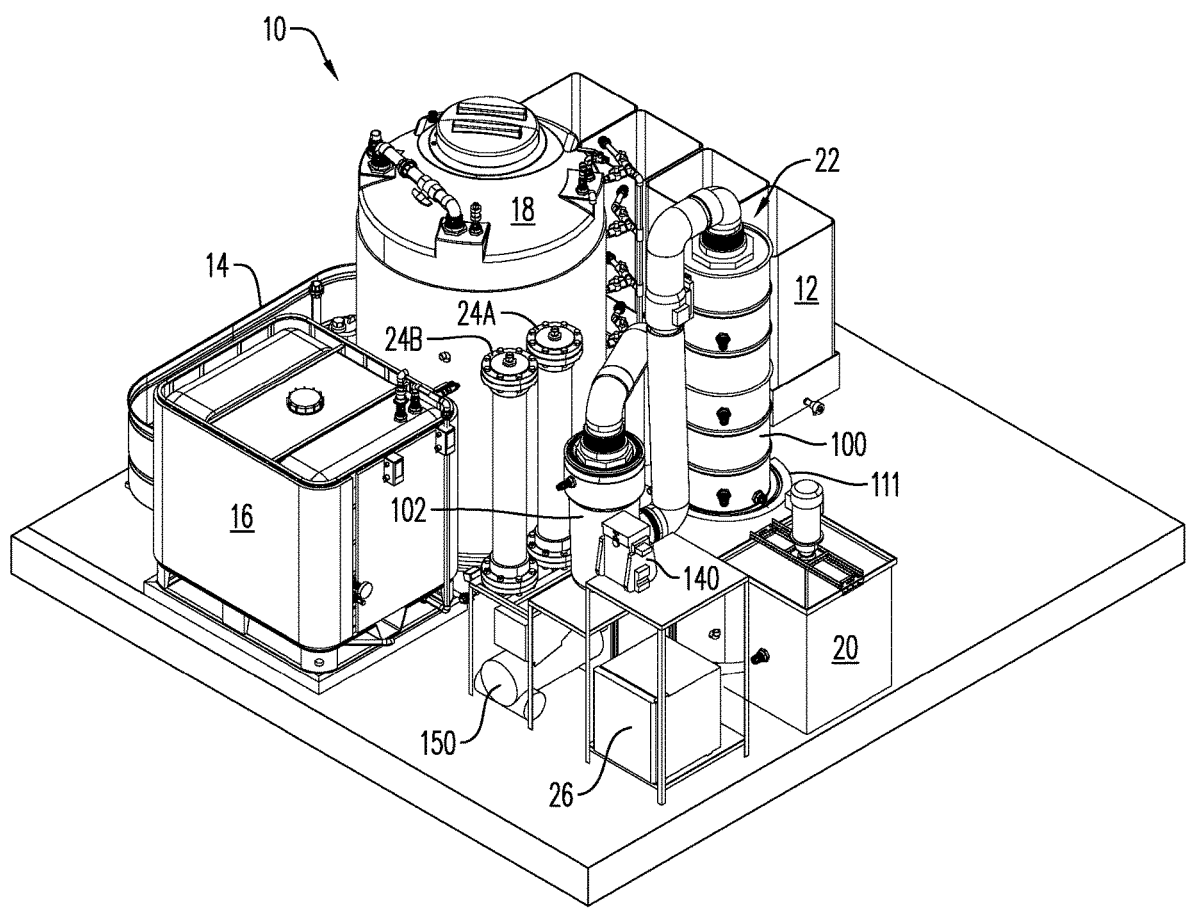
FIG. 1B is another plan view of the System of FIG. 1A.
Figure 2:
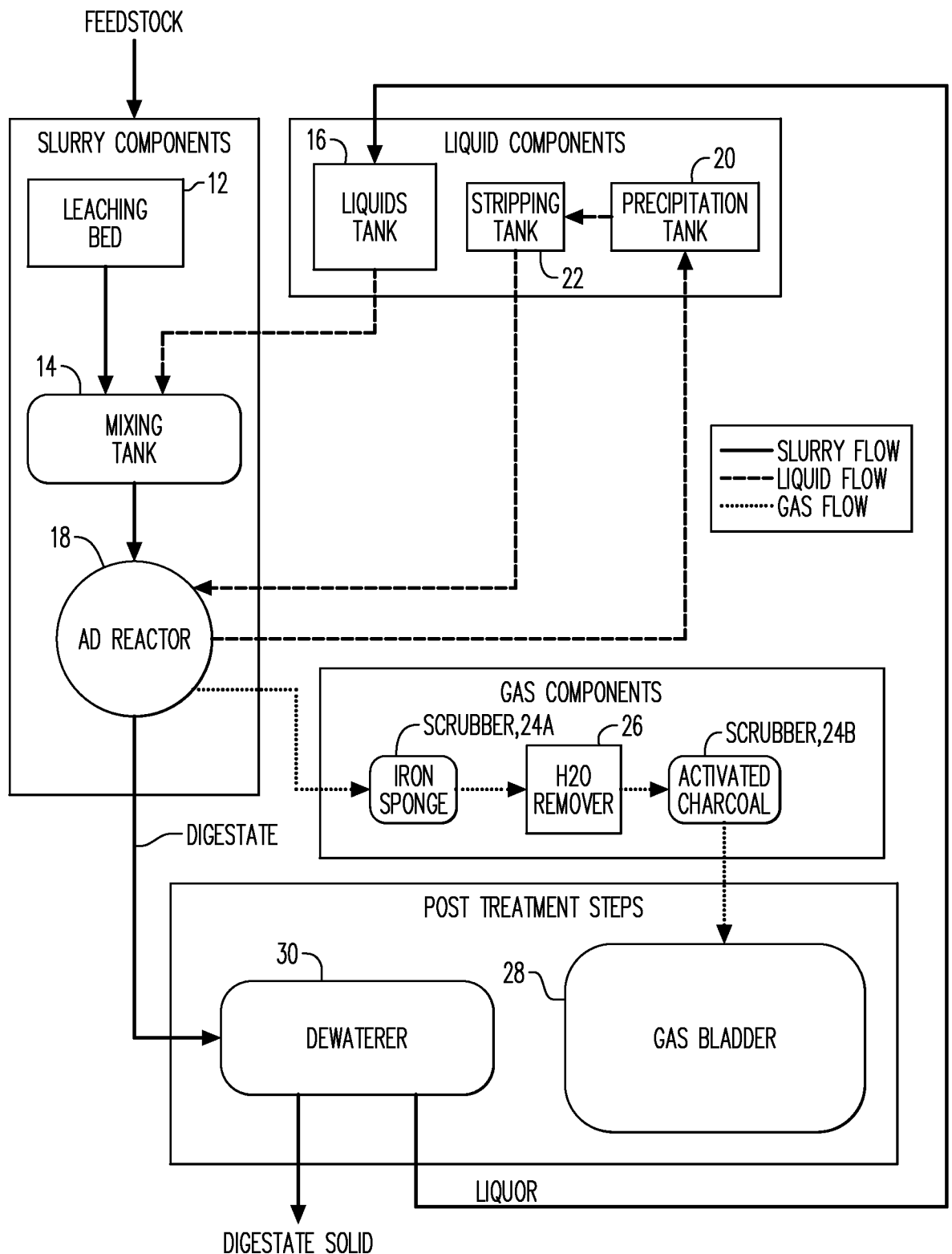
FIG. 2 is a flow diagram of the invention shown in FIG. 1.

Referring, for example, to FIG. 2, the primary components of the System include: (1) a leaching bed; (2) a liquids tank; (3) a mixing tank; (4) an anaerobic digester reactor; (5) a precipitation tank; (6) a stripping tank; (7) an $H_2S$ scrubber; (8) an $H_2O$ remover; (9) a gas bladder; (10) a dewaterer; and (11) a flare system (not shown). Referring to FIGS. 1 and 2, the invention is, therefore, directed to a modular anaerobic digestion point-of-waste to renewable energy system 10 for converting an organic feedstock material into a biogas and a digestate. This apparatus and method comprise a leaching bed 12 adapted to receive the organic feedstock material and water to remove inhibitory nutrients; a mixing tank 14 adapted to receive from the leaching bed the leached feedstock; a liquids tank 16 adapted to provide liquids to the mixing tank; a means for macerating the feedstock and the liquids in the mixing tank into a feedstock slurry; an anaerobic digester reactor 18 wherein the feedstock slurry is pumped from the mixing tank 14 into the anaerobic digester reactor 18 and wherein anaerobic digestion takes place to convert the feedstock slurry into the biogas and the digestate; a precipitation tank 20 and a stripping tank 22 wherein a portion of the feedstock slurry in the anaerobic digestion reactor 18 is pumped first into the precipitation tank 20 and then into the stripping tank 22, the precipitation tank 20 and the stripping tank 22 are adapted to clean the feedstock slurry of at least phosphorus and ammonia, wherein the cleaned feedstock slurry is pumped back into the anaerobic digester reactor 18; hydrogen sulfide scrubbers 24A and 24B adapted to receive the biogas wherein the hydrogen scrubber removes hydrogen sulfide from the biogas; a water remover tank 26 adapted to receive the biogas from hydrogen sulfide scrubber 24A wherein water is removed from the biogas; a gas bladder 28 adapted to receive the biogas from the hydrogen sulfide scrubber 24B wherein the biogas is stored for subsequent use; a dewaterer 30 adapted to receive the digestate from the anaerobic digester reactor wherein the digestate is dewatered for subsequent use; and wherein the system is adapted to be located at the point-of-waste and is adapted to be scaled to handle the volume of organic material by alternating the size of the components thereof. Each of these components will now be described in further detail.

Figure 3A:
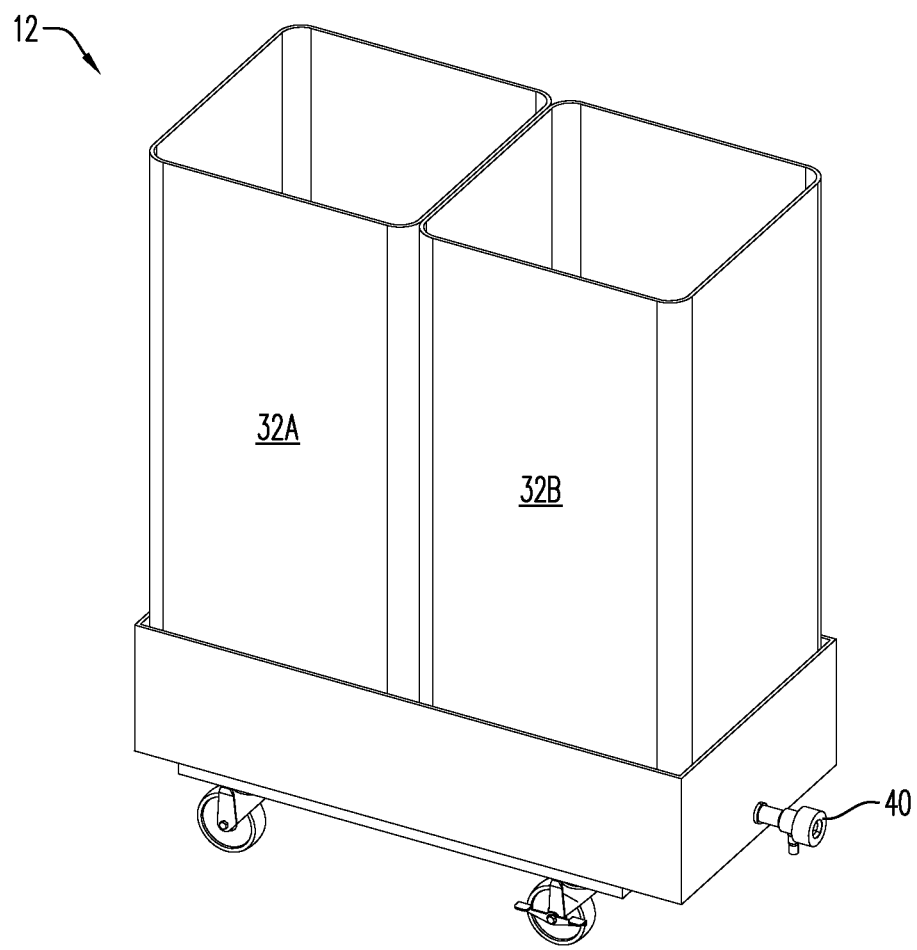
FIG. 3A is a perspective view of the leaching bed of FIG. 1.
Figure 3B:
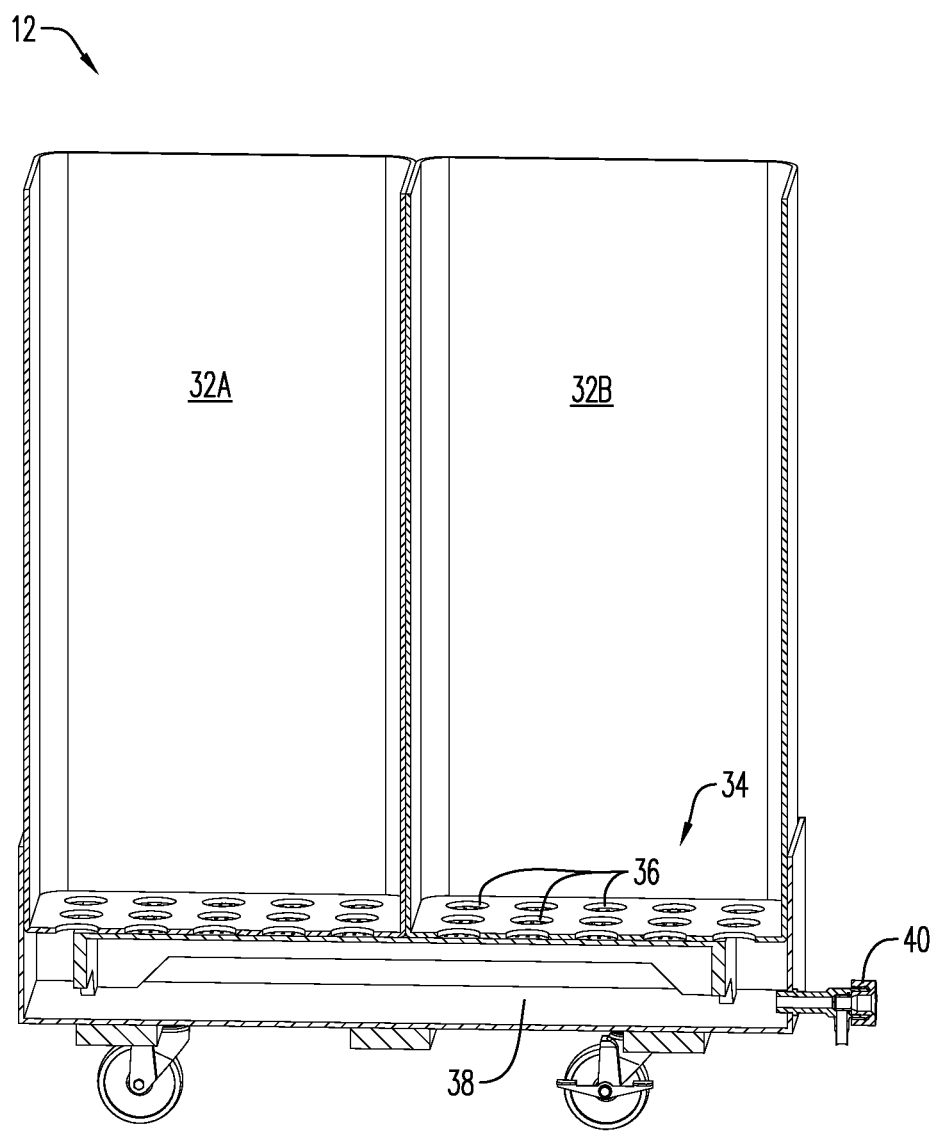
FIG. 3B is a cross-section of the leaching bed of FIG. 3A.

The leaching bed 12 is seen in FIGS. 1-3. The leaching process serves to prepare feedstocks with high concentrations of inhibitors such as humic acids and/or potassium, e.g., chicken manure, for anaerobic digestion by removing inhibitory species via a leaching process. The feedstock to be used in a batch is loaded into the leaching bed. Water is then gently added to columns 32A,32B of organic matter (not shown) and allowed to leach through the material, solubilizing inhibitors as it proceeds. It is understood that any number or size of columns 32 may be used depending on varying factors, including the scale of the process, the nature of the feedstock and the like. After leaching, a liquid rich in inhibitors, i.e., the leachate, is eluted from the bottom 34 of the leaching bed through pores 36 where it is captured in a separate tank 38 having a drain port 40 for recovery. Proper operation of this process will yield a feedstock with reduced inhibitor and salt content, rendering it more available for anaerobic digestion upon introduction into the anaerobic digester reactor 18. The leachate can also be used as a fertilizer due to its rich potassium content or can be transferred into the precipitation tank 20 to be treated for the removal of phosphorus.

Figure 5A:
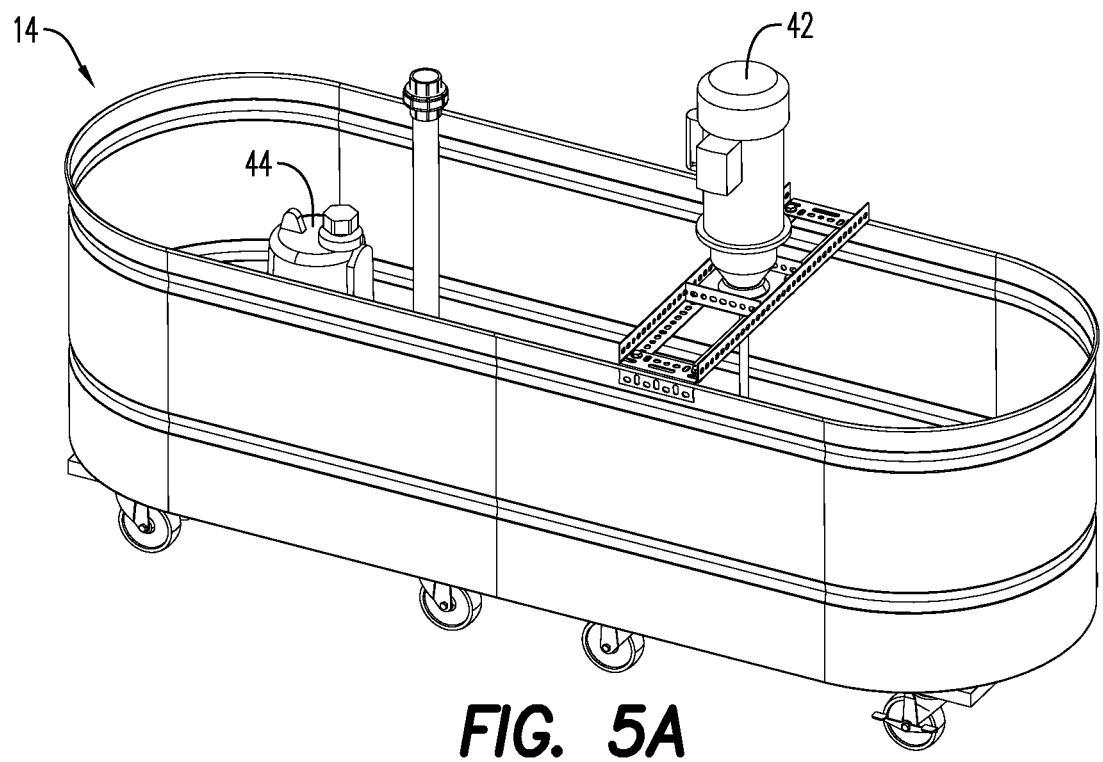
FIG. 5A is a perspective view of the mixing tank of FIG. 1.
Figure 5B:
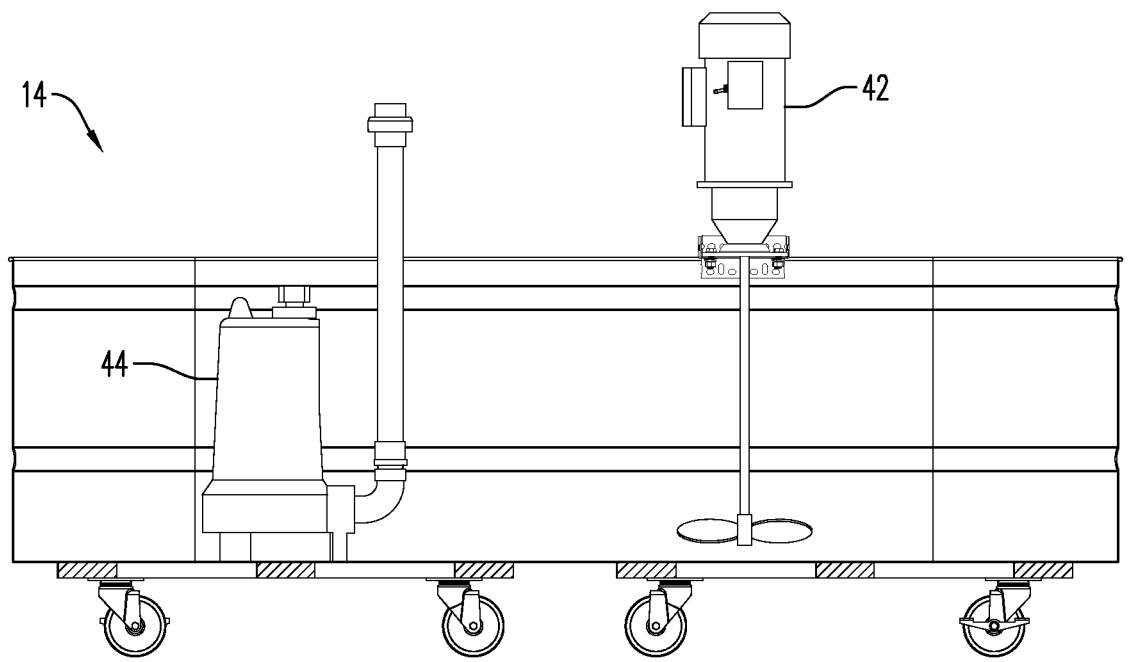
FIG. 5B is a cross-section of the mixing tank of FIG. 5A.

The mixing tank 14 is seen in FIGS. 1, 2 and 5. This component of the System mixes the feedstock with liquids from the liquids tank 16 to create a feedstock slurry with the desired concentration of total solids (TS) and breaks down the average particle size so system pumps can process a feedstock slurry. This is also effective at separating rocks, twigs, fibers, and other bodies from the manure which can clog pumps before introducing the feedstock slurry into the AD reactor. In some System configurations, the capabilities of this tank may be installed into the AD reactor. The mixing tank includes a rotary mixer 42 for mixing the feedstock and the liquids and a maceration pump 44 on the bottom of tank which is used to pump material into the anaerobic digester reactor.

Accordingly, once the feedstock has been through the leaching process, it is moved into the mixing tank 14 where it is combined with liquids from the liquids tank 16 to create a feedstock slurry with the percentage total solids ratio that is required for anaerobic digestion, depending on the organic material to be used. As discussed below, there is a water totalizer (not shown) installed along the line from the liquids tank to the mixing tank which accurately accounts for how much liquid is being introduced into the mixing tank.

While in the mixing tank, the two phases, i.e., solids and liquids, are blended together using the rotary mixer 42 to create the feedstock slurry. The maceration pump 44 further combines the two phases while providing a means of transferring the prepared feedstock slurry into the AD reactor. Furthermore, this pump acts as a way to reduce the odds of failure for other pumps in the system by (a) breaking down large solids and (b) serving as a way to remove components of the feedstock which may damage the less robust pumps encountered during the retention time of a batch, e.g., rocks, twigs, large fibers and the like. In situations where multiple tanks are required to handle the volume of waste on hand, a series of pipes may be installed to direct the feedstock slurry into different reactors operating in series.

Figure 4A:
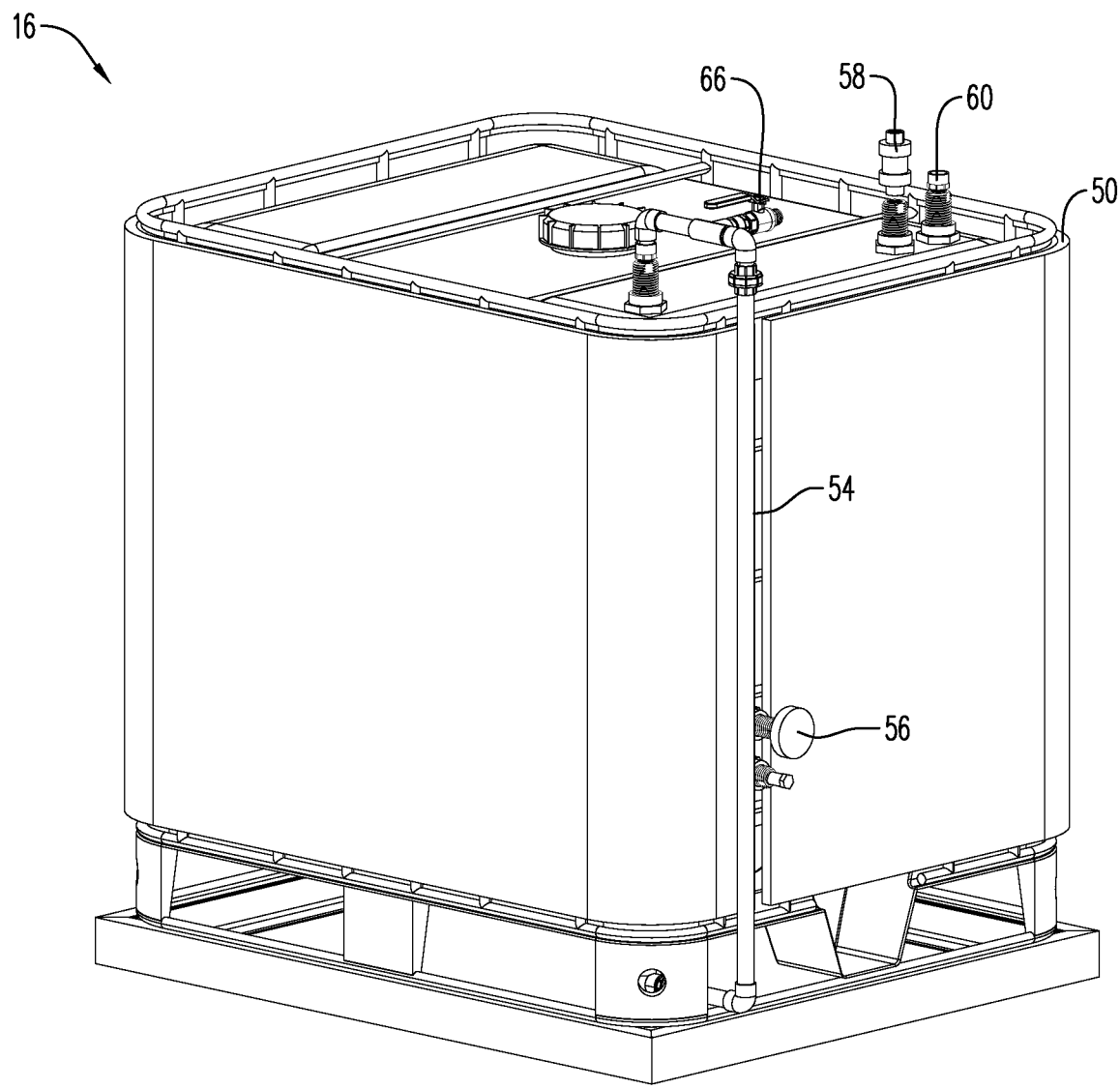
FIG. 4A is a perspective view of the liquids tank of FIG. 1.
Figure 4B:
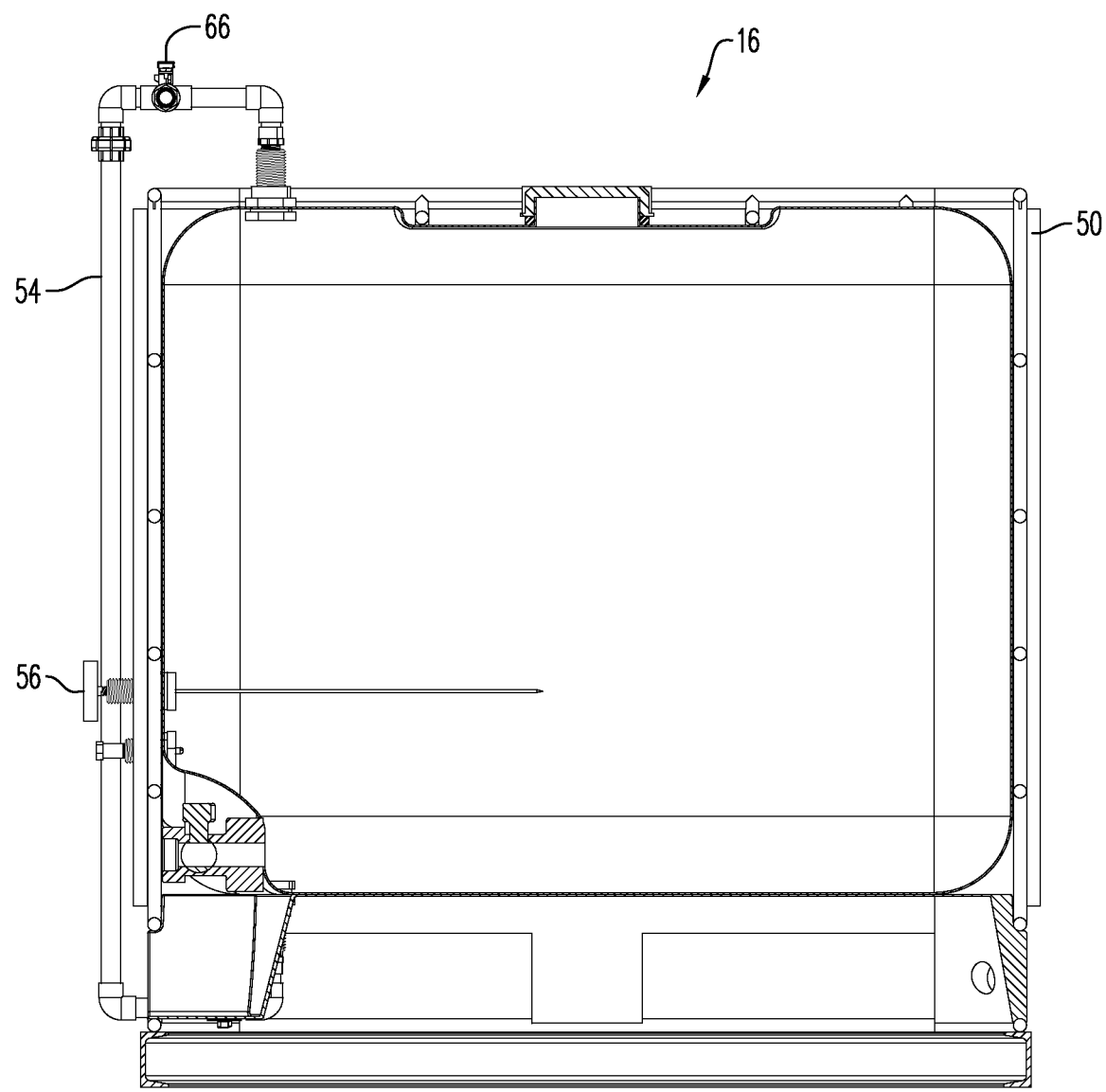
FIG. 4B is a cross-section of the liquids tank of FIG. 4A.

The liquids tank 16 is shown in FIGS. 1, 2 and 4. This tank stores and heats liquid or liquor between batches for use in feedstock preparation in the mixing tank. Features of this tank include (1) external electric heat blanket 50; (2) an insulation material (not shown) on the outside of the heat blanket; (3) a water level tube 54 on the side to visually assess the liquid level inside the liquids tank; (4) a temperature sensor 56 on bottom of tank; (5) a biogas collection port 58; (6) a fill port 60; (7) an outlet port (not shown) with a liquid flow meter (not shown); (8) a pressure equalization valve 66 to equalize the pressure of tank with the atmosphere when liquids are loaded and unloaded; and (9) transfer pumps (not shown) to move liquids between components, e.g. from and to the mixing tank 14 and anaerobic digester reactor 18.

The liquids tank holds water and/or liquor which has been heated by an electric blanket to approximately 100° F. The methanogens within the liquor are microorganisms that feed on organic material and create methane as a byproduct of their metabolism. The volume level indicator 54 and temperature sensor 56 are used for monitoring the amount and temperature of the liquid before use in feedstock preparation. The transfer pump (not shown) pulls liquid from the bottom of the tank to load into the mixing tank. The flow meter (not shown) is connected along this pipeline to gauge how many gallons have been transferred. The liquids line has a series of valves that allow the user to control where liquids are routed, enabling direct addition to the AD reactor 18, if desired.

Figure 6A:
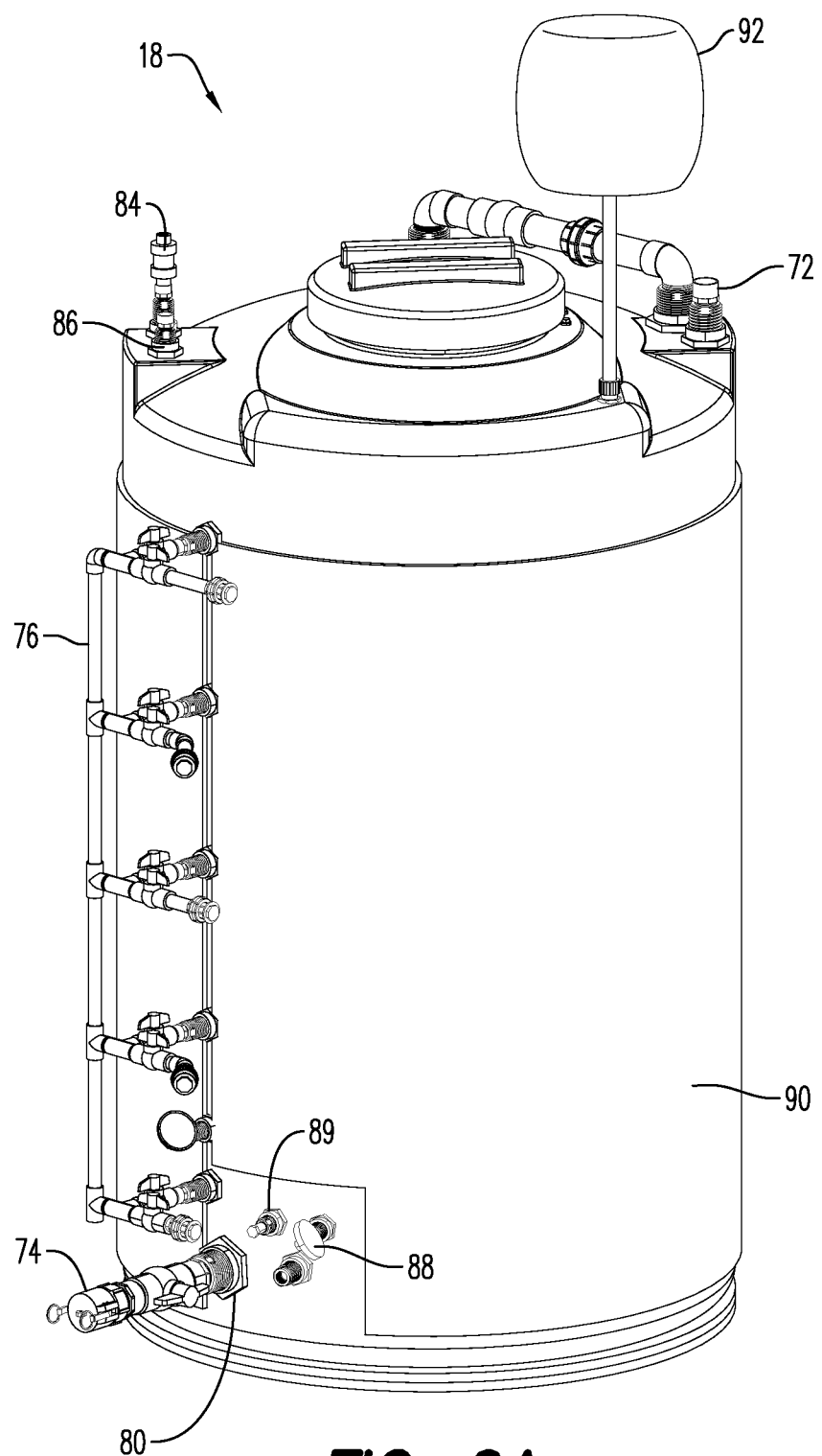
FIG. 6A is a perspective view of the anaerobic digester reactor of FIG. 1.
Figure 6B:
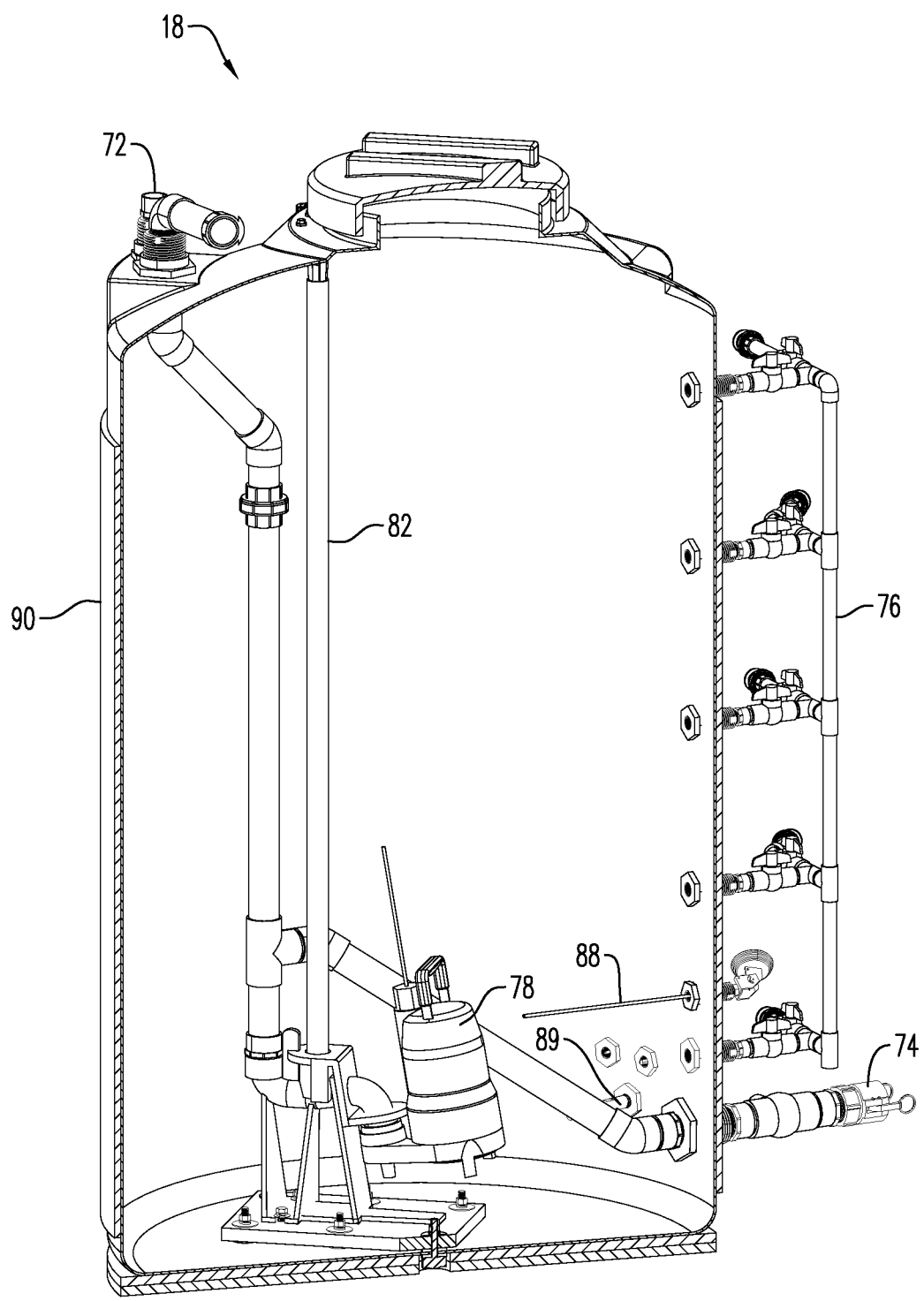
FIG. 6B is a cross-section of the anaerobic digester reactor of FIG. 6A.

The anaerobic digester reactor 18 is shown in FIGS. 1, 2 and 6. The anaerobic digestion occurs in the AD reactor. The AD reactor allows for both batch loading and continuous loading. Prior to digestion, a mature microbial population is added to the AD reactor from a previous AD batch which will facilitate digestion for the subsequent cycle. The AD reactor features include: (1) a feedstock slurry inlet port 72 which is used to load the AD reactor with feedstock slurry from mixing tank 14 after preparation of the feedstock slurry; (2) a discharge valve 74 used to expel digestate from the AD reactor during the unloading process; (3) a level indicator 76 which visually assesses the height of materials inside the AD reactor and permits a sampling of the AD slurry during operation; (4) an effluent pump 78 inside the reactor used to pump digested material, especially settled solids, from the reactor using the outlet port 80 when digestion is complete; internally mix the material during digestion by circulating settled solids into the top of the reactor to break down crust which forms an internal mixing loop; and a guiderail 82 installed to raise and lower effluent pump for maintenance; (5) a biogas collection port 84; (6) a biogas pressure equalization port 86; (7) temperature probe 88 which probe is placed in the feedstock slurry; (8) a heating blanket 90 which includes a temperature sensor (not shown) for automatic start up and stop, located in headspace of the reactor; and (9) a bladder 92 (not shown in FIG. 6B) filled with biogas and which compresses during liquid transfer to equalize pressure and prevent buckling of the AD reactor.

While the feedstock slurry is in the AD reactor, microorganisms initiate anaerobic digestion, a process which breaks complex organic molecules down into volatile fatty acids which methanogens can target to begin the methanogenic process. The proceeding of methanogenesis manifests via the production of methane in the evolved biogas. The production of biogas from a healthy System is best described as a bell curve in terms of production with respect to time. The time prior to the bell-shaped biogas production is known as the lag phase which represents the period of microbial acclimation to a new feedstock and solution conditions. As biogas production begins, the highest point of the bell curve represents the period of highest methane production. As the organic matter within the feedstock slurry is exhausted, the biogas production gradually tapers off until no more methane can be produced. By optimizing the retention time of each batch, the period of peak biogas production can be maximized to yield the most efficient recovery of methane during system operation.

The effluent pump 78 located inside of the AD reactor mixes the material during digestion by circulating settled solids from the bottom of the reactor into the top to break down crust formed at the interface between the media and headspace. This enables an internal mixing loop.

The AD reactor 18 is also equipped with solution monitoring probes 88 and 89 to report the temperature and pH, respectively, of the feedstock over time. This is important to ensure that the temperature of about 95-100° F., and a pH of about 7.2, remain within the values most conducive to methanogenesis.

As biogas is produced, its composition is measured at a sampling port (not shown) before being fed into the bottom of the biogas treatment system as discussed hereafter.

Figure 7A:
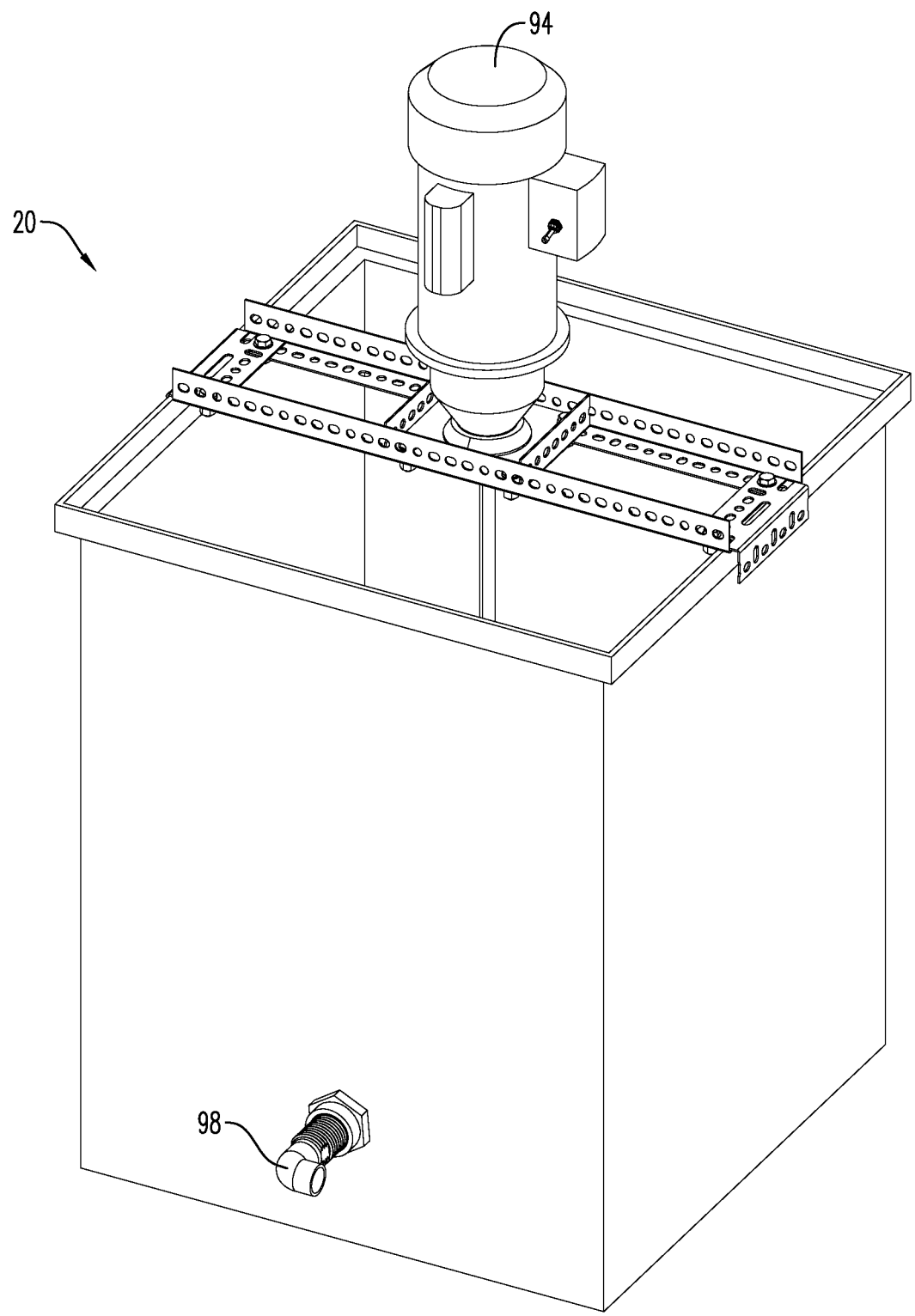
FIG. 7A is a perspective view of the precipitation tank of FIG. 1.
Figure 7B:
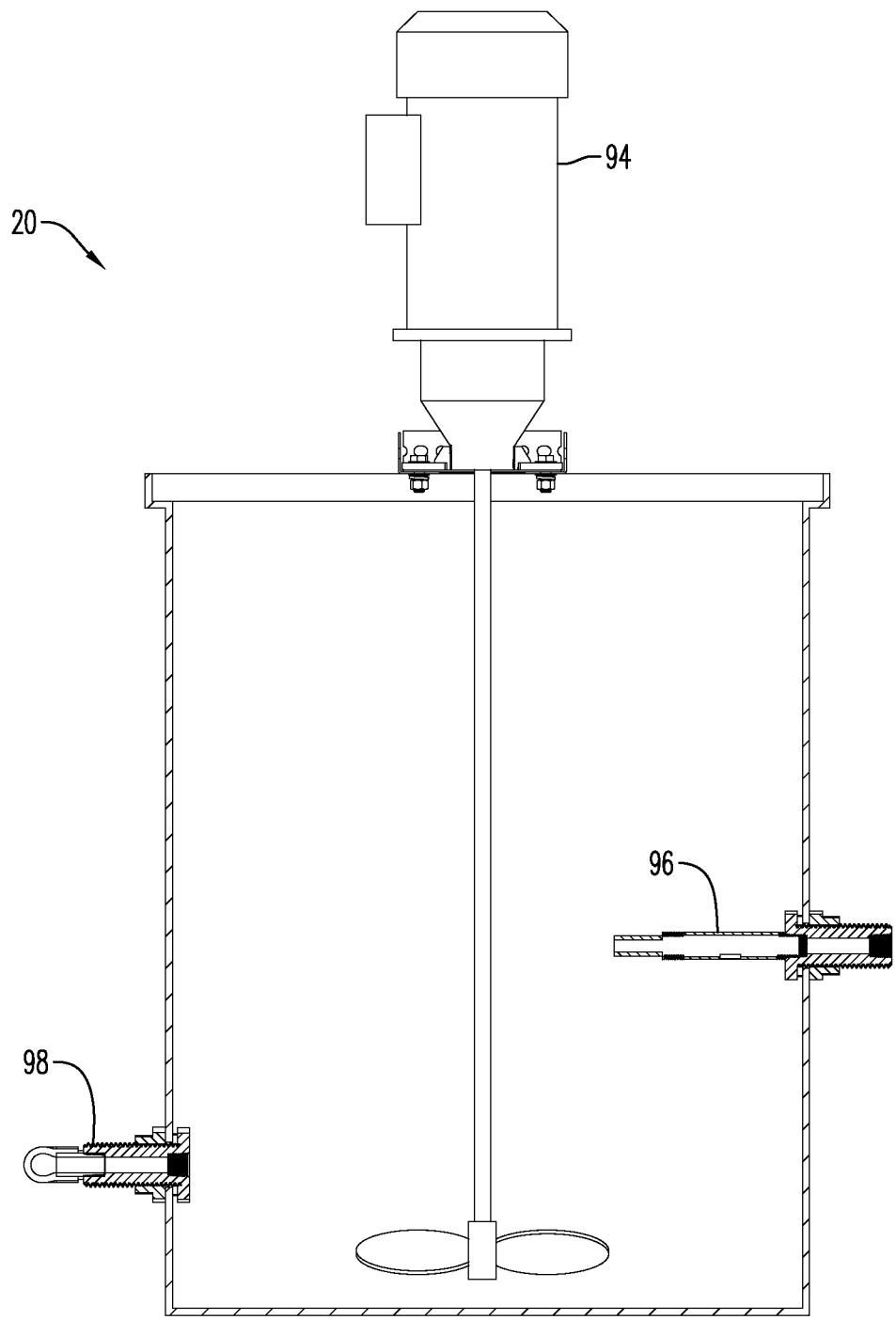
FIG. 7B is a cross-section of the precipitation tank of FIG. 7A.
Figure 8A:
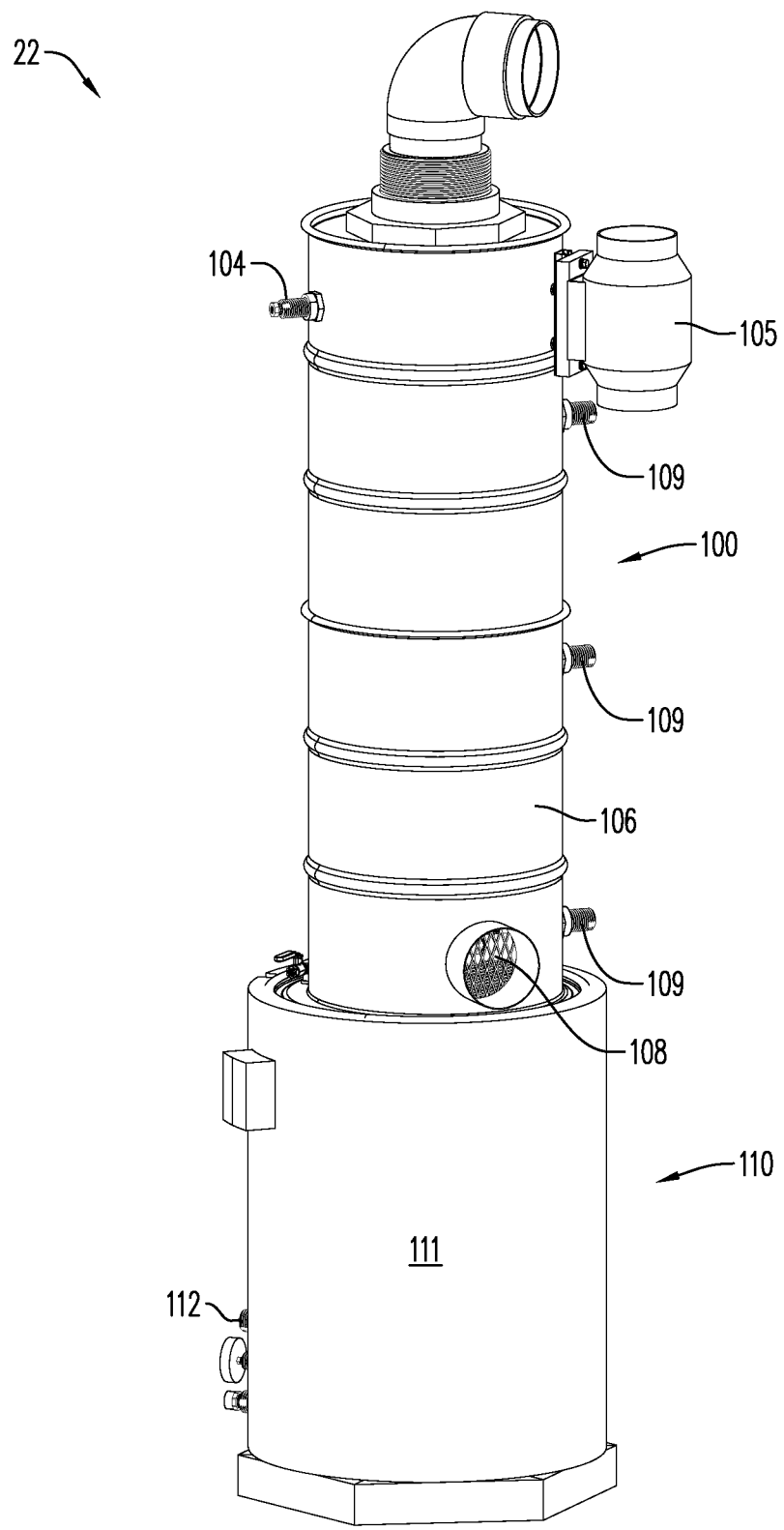
FIG. 8A is a perspective view of the stripping tank of FIG. 1.
Figure 8B:
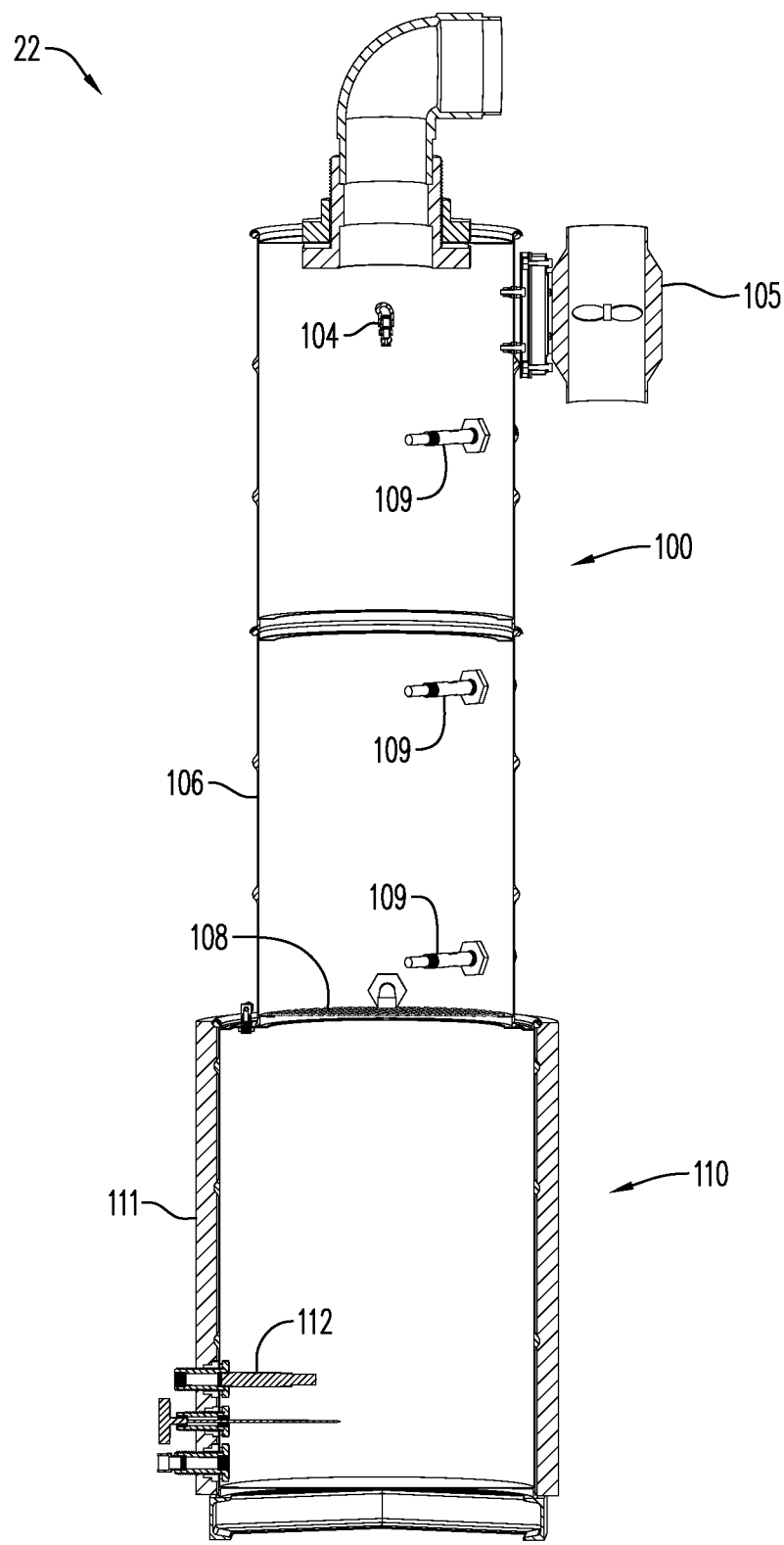
FIG. 8B is a cross-section of the stripping tank of FIG. 8A.
Figure 8C:
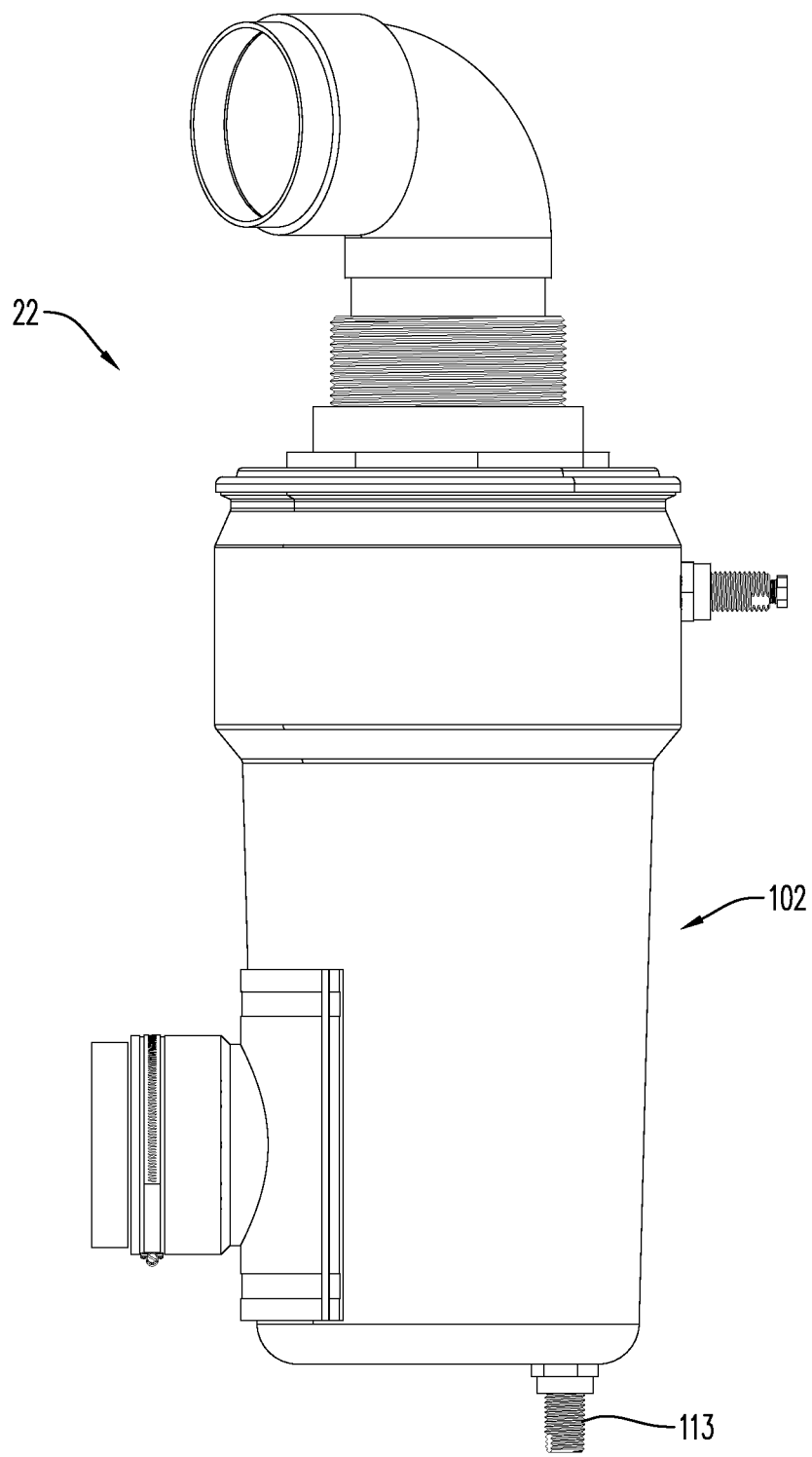
FIG. 8C is a perspective view of the ammonia stripping dropoff of the stripping tank of FIG. 1.
Figure 8D:
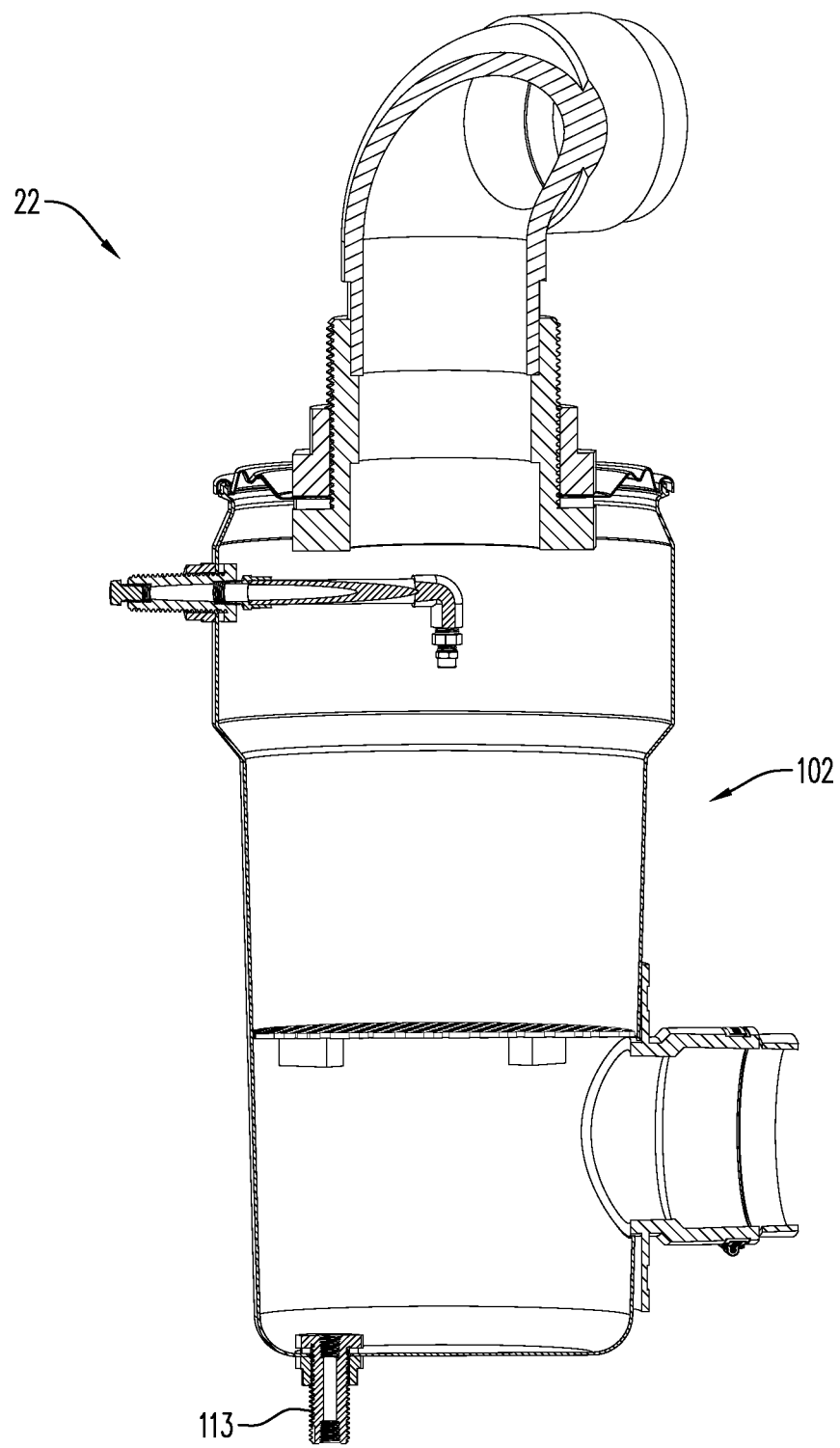
FIG. 8D is a cross-section of the ammonia stripping dropoff of the stripping tank of FIG. 8C.

The precipitation tank 20 is shown in FIGS. 1, 2 and 7. Phosphate is captured from the feedstock slurry or leachate to reduce nutrient runoff from cake when used as a fertilizer. Raising the pH via $CO_2$ off-gassing or adding lime or slaked lime facilitates phosphate precipitation. The treated leachate is used as a potassium fertilizer while treated feedstock slurry is either transported to the stripping columns for ammonia removal or sprayed back into the AD reactor to pick up more phosphate for subsequent precipitation treatments. The precipitation tank includes a rotary mixer 94, a pH probe 96 and an outlet port 98.

Typically, precipitation treatment is the first step in the precipitation and stripping process. Feedstock slurry is pumped in from the AD reactor into the precipitation tank where it is either bubbled with air to allow $CO_2$ to off-gas or combined with lime, resulting in an increase in pH. Treatments will continue until a pH of about 9 is achieved, indicated by the pH probe 96 equipped in the precipitation tank. The feedstock slurry within the tank is then mixed and allowed to rest as solids gradually precipitate from solution and settle at the bottom of the tank. The treated slurry will finally be pumped out and passed through the stripping pickup column 100 of stripping tank 22. Importantly, this entire process can be scaled based on the volume of waste being processed at any given site.

The stripping tank 22 is shown in FIGS. 1, 2 and 8. The stripping tank includes a stripping pickup column 100 and a stripping dropoff tank 102. The column removes species such as ammonia, hydrogen sulfide, and carbon dioxide and provides control over the solution parameters during a batch and improves the digestion of high-nitrogen and high-sulfur organic material. The treated feedstock slurry passes through solid media (not shown) of the stripping pickup column 100 to allow ammonia to escape from solution. Air will pass through the stripping pickup column 100 to transport ammonia into the stripping dropoff tank 102 where it will be captured by sulfuric acid as ammonium sulfate. The same operation may be used to remove hydrogen sulfide ($H_2S$) or carbon dioxide from solution by filling the stripping dropoff tank 102 with a base. This reduces nitrogen in the final cake and/or liquor when used as a fertilizer. The stripping dropoff tank 102 may also comprise two stripping dropoff tanks 102: one filled with acid, and one filled with base. This will allow both acidic and basic constituents of the AD slurry to be removed via the stripping process.

More specifically, stripping pickup is the first step in the stripping of ammonia, hydrogen sulfide, or carbon dioxide. The inlet valve 104 is located at the top of the column 100 above a packed column 106 of solid media (not shown) which are held above a wire mesh 108 with air flowing upwards from the fan 105 through them. The solid media are designed to maximize the exposed surface area of liquid passing through the column 106, thus offering the highest potential for gaseous compounds, e.g., ammonia, to escape from solution within the flowing air. The stripping pickup column 100 is equipped with pH sensors 109 at the top, middle, and bottom of the tank to monitor the pH of the slurry as it is stripped of dissolved gases during transport through the column. After being stripped, the feedstock slurry is sequestered in a holding tank 110 beneath the stripping pickup column which is heated by an electric blanket 111 and includes a pH sensor 112 to ensure that pH has dropped to near neutral levels before reintroduction into the AD reactor. If pH is too high, the transfer pump may be used to pass the volume of feedstock slurry through the stripping pickup column an additional time, a process which is repeatable for as many cycles as are needed to reach the desired pH.

The air carrying the gas which was stripped from the stripping pickup column 100 enters the stripping dropoff tank 102. The dropoff tank includes solid media which have been coated in either sulfuric acid or sodium hydroxide. As noted above, two dropoff tank 102 may be used, each filled with either acid or base to permit the routing of gas through either tank, thus enabling both treatments in-line with the process. When combined with ammonia, this sulfuric acid forms ammonium sulfate, a common nitrogen-based liquid fertilizer used on farms. Hydrogen sulfide forms NaHS and $Na_2S$ when reacted with sodium hydroxide, which are non-harmful compounds with potential use as sulfur-based fertilizers. Carbon dioxide is captured as carbonic acid which is a non-harmful compound which can be easily disposed of and represents a form of carbon capture from the system. These byproducts are easily recovered via a sampling port 113 equipped at the bottom of the stripping dropoff tank. Acid or base is cycled through the solid media using a pump, being replenished whenever the current coating is neutralized from the capture of gaseous species produced during anaerobic digestion.

To pass aliquots of liquid from the AD reactor through the precipitation and stripping tanks, a transfer pump is piped between the two tanks. This pump is rated to efficiently move roughly 10% of the total feedstock volume through the precipitation and stripping system, and two of these aliquots can exist within the system at any given time. Furthermore, the System is designed such that feedstock slurry from the AD reactor can be transferred to the precipitation tank 20, stripping tank 22, or between these latter two components as needed.

Figures 9A, 9B:
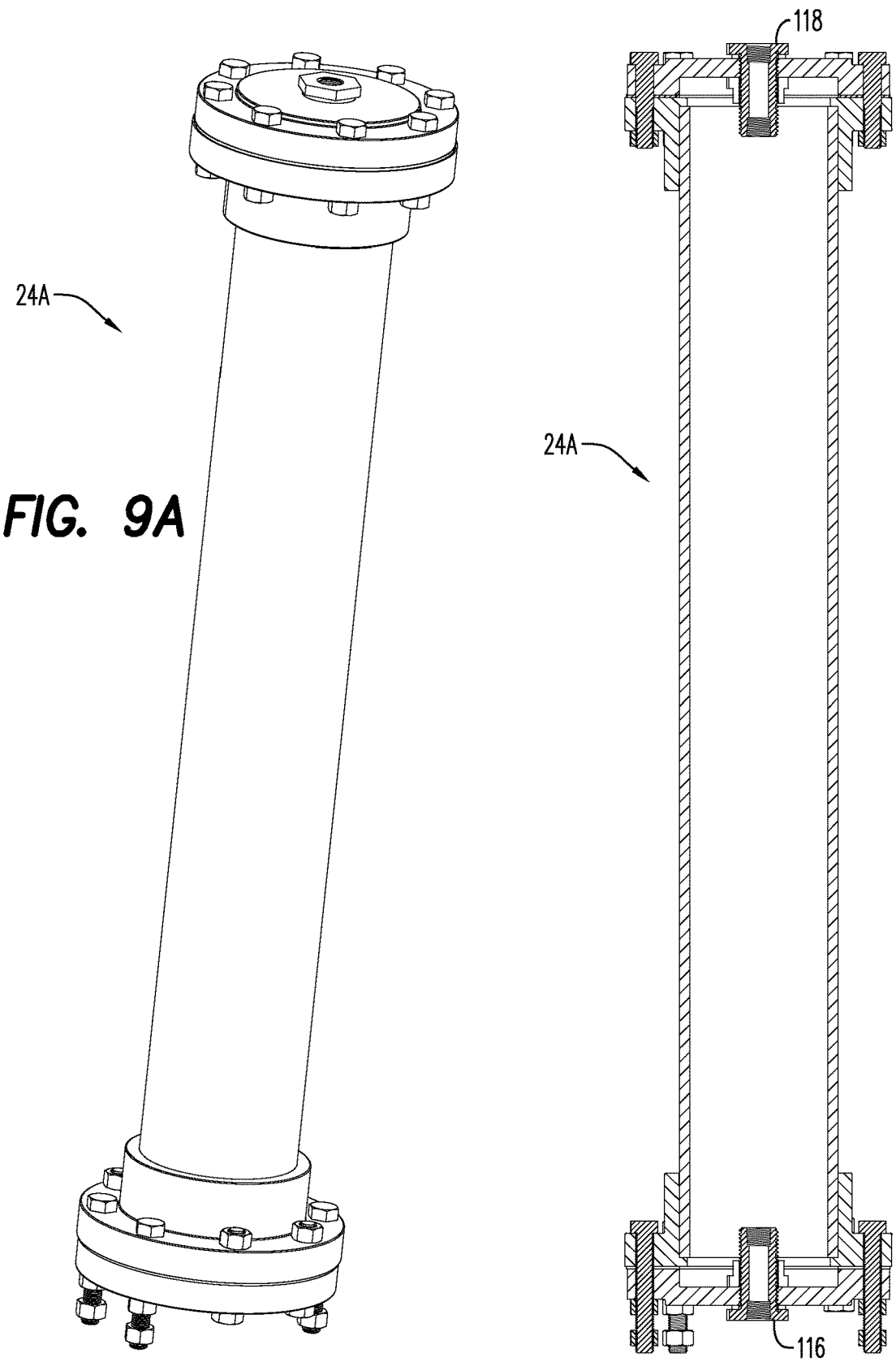
FIG. 9A is a perspective view of one of the $H_2S$ scrubbers of FIG. 1.
FIG. 9B is a cross-section of the $H_2S$ scrubber of FIG. 9A.
Figure 10A:
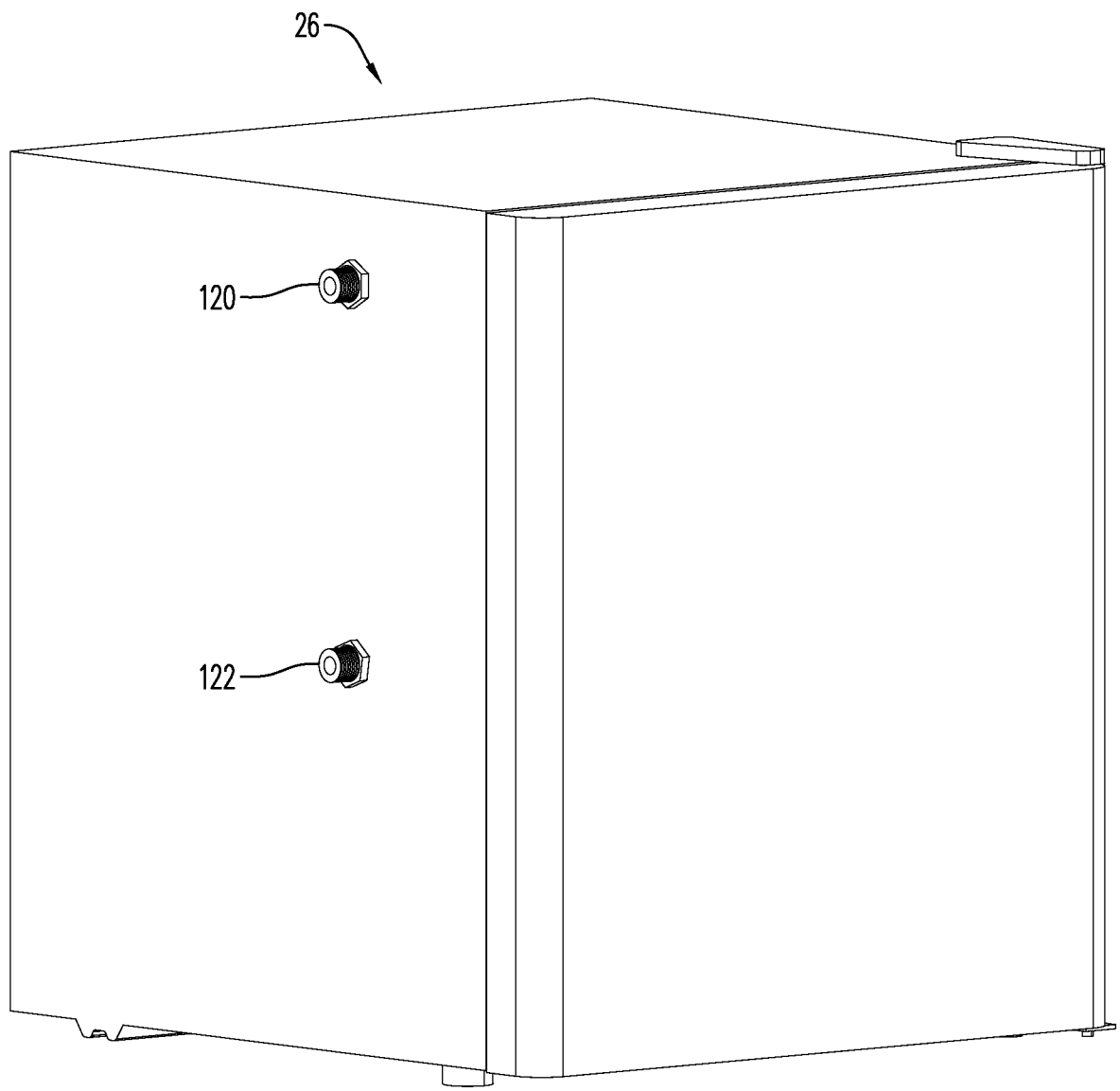
FIG. 10A is a perspective view of the water remover of FIG. 1.
Figure 10B:
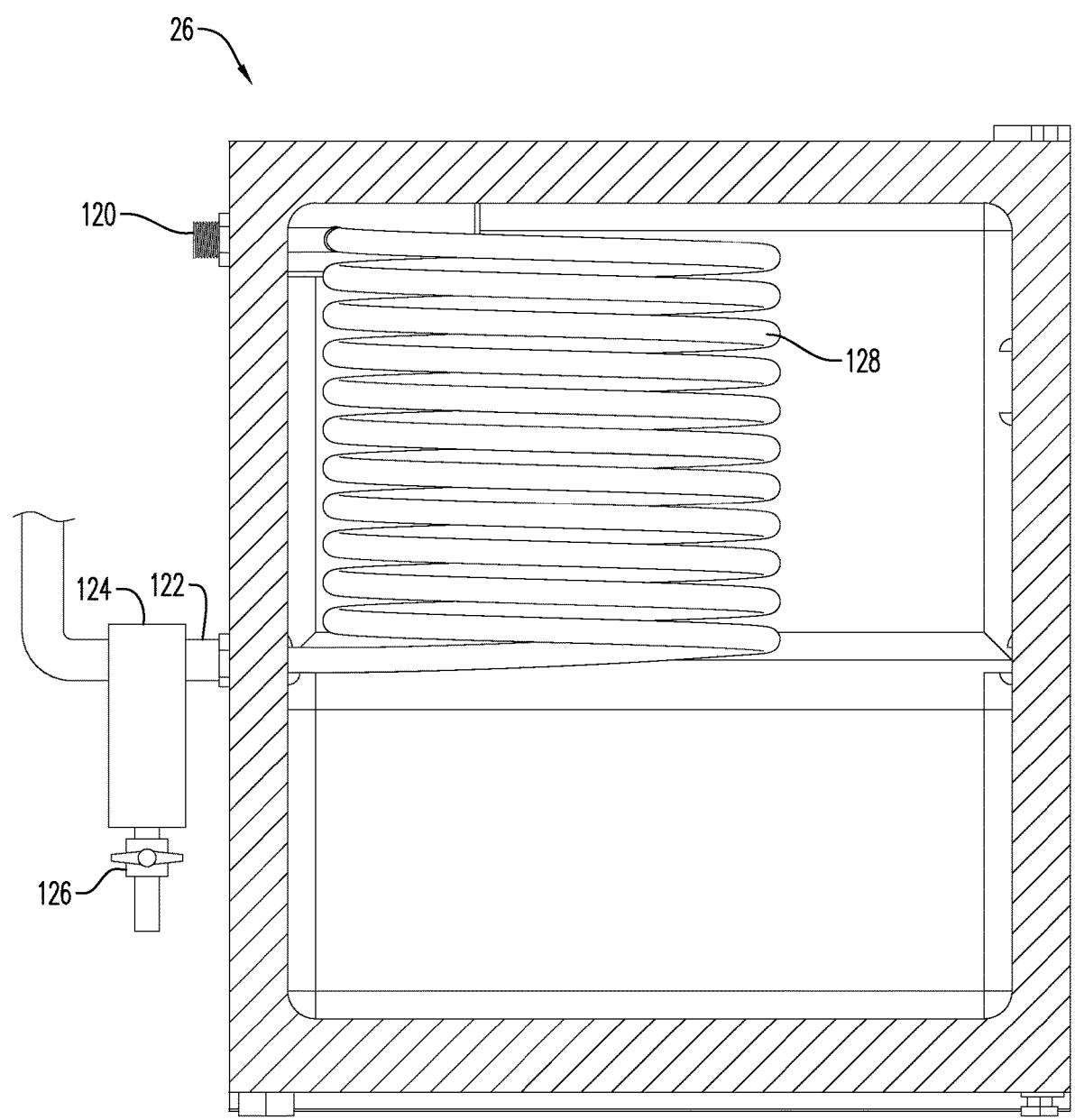
FIG. 10B is a cross-section of the water remover of FIG. 10A.

The $H_2S$ scrubber 24A is shown in FIGS. 1, 2 and 9 and the water remover 26 is shown in FIGS. 1, 2 and 10. The $H_2S$ scrubbers 24A and 24B are substantially the same in construction as shown in FIGS. 9A and 9B. The scrubbers 24A, 24B and $H_2O$ remover 26 work in conjunction to remove $H_2S$, a corrosive component of the gaseous mixture, from the biogas. As shown in FIG. 2, the biogas is first treated in iron sponge scrubber 24A; the treated biogas transferred to $H_2O$ remover 26; and the treated biogas thereafter transferred from $H_2O$ remover to activated charcoal scrubber 24B, as described hereafter. Scrubbers 24A and 24B are comprised of two scrubber units, namely, (1) an iron scrubber 24A which includes an iron sponge such as iron infused chips packed in the column (not shown) kept basic by NaOH and having a pH of 10-12, this pH is necessary for maintaining $H_2S$ capture and aqueous solubility as HS—; and (2) a scrubber 24B having activated charcoal packed in the column which provides for the non-covalent bonding of small molecules, e.g., $H_2S$, with the porous surface of activated charcoal. The scrubber 24A includes an inlet port 116 for receiving the biogas to be treated and an outlet port 118 for discharging of the treated biogas. In scrubber 24B, the inlet port is at the top of the scrubber and the outlet port is at the bottom of the scrubber.

Referring to FIG. 10, the $H_2O$ remover 26 cools the biogas, causing condensation of water, which is captured by a water separator and drained off through a no-air-loss drain valve. In the alternative, a desiccant dryer may be used to remove water from the biogas via adsorption. This component includes (1) ports 120 and 122, namely, a biogas inlet 120, a biogas outlet 122, and a water separator 124 and drain valve 126 (not shown in FIG. 10A). There is a steel tube 128 coiled inside connecting the biogas inlet 120 to the biogas outlet 122.

After leaving the $H_2S$ scrubber 24A, the gas travels into the $H_2O$ remover 26. The $H_2O$ remover is a cooled chamber through which the gas travels via a spiraled metal coil 128. During transport, water from the gas condenses and collects in a water separator (not shown) located at the bottom of the coil. Once a sufficient volume of water has been collected, the water separator automatically drains the condensate out of the line to conclude its removal.

Referring again to FIG. 2, after the biogas leaves the $H_2O$ remover 26, it travels to the activated charcoal $H_2S$ scrubber 24B. The activated charcoal offers a porous, high surface area media which $H_2S$ can adsorb to, effectively removing it from the gaseous mixture. After leaving the activated charcoal $H_2S$ scrubber 24A, a gas sampling port (not shown) in the line enables the measurement of $H_2S$ levels to ensure the biogas is properly cleaned and ready for subsequent use.

The biogas then travels through a gas meter 140 along the line to track the produced volume of biogas before being stored in the gas bladder 28. Here, the cleaned biogas is available to be drawn out when needed and run through a compressor that will provide the proper pressure to function with any engine the gas is intended to fuel.

The gas bladder 28 is shown in FIG. 2. The gas bladder stores the biogas. In the alternative, a compressed tank may be used to increase the storable volume of biogas. "Gas bladder" is used herein to refer to all storage means for the biogas. The gas bladder includes a port out having adapters and connections for gas line from totalizer (quantifies volume of gas produced) and a line going to a compressor 150, and a sensor which functions as a pressure gauge.

The flare system (not shown) may be used should the biogas need to be expelled from the bladder 28, a flare system is incorporated into the design to allow for safe disposal. The circumstances for this action include the following, (1) should the bladder fill to an unsafe volume and pressure; or (2) should the System be dismantled and moved; or (3) should the System present a leak that is unable to be repaired without biogas expungement.

Referring to FIG. 2, the digestate is removed from anaerobic digester 18 at discharge port 74 and runs through a hose to dewaterer 30. The dewaterer 30 may comprise a screw press or like device to remove the water from the digestate. The digestate is treated and may thereafter form a solid, e.g. cake, or a liquid for use as a fertilizer as discussed hereafter.

This System has been found quite useful when used as described herein. Thus, the System allows for the production of biogas at a scale designed to be accessible to smaller commercial and residential markets. This can be used to alleviate energy demand on site using waste streams produced on site, thus reducing reliance on utility vendors while also offering an option for waste management and reduction. Nutrients may be isolated from the feedstock as soil amendments. The System reduces organic waste currently discarded into landfills. The cake recovered after AD treatment can be used as a fertilizer, even in regions where phosphorus and nitrogen release is restricted. The cake is a nutrient rich and customizable soil amendment. The biogas, a renewable natural gas, can be utilized as a fuel. Ammonium sulfate may be used as a nitrogen-rich liquid fertilizer. In regions where permissible, solid calcium phosphate fertilizer may be sequestered which can be reapplied to fields in a controlled manner to supplement soils with phosphorus. The leachate obtained during the initial leaching step may be used separately as a means to add nutrients to soils, depending on constituents removed, e.g., potassium may be used as a potash fertilizer. The liquor isolated from the slurry may be used to promote the efficient anaerobic digestion of subsequent batches of feedstock processed by the System.

The prior art AD systems serving farms and individual residents have failed to make themselves accessible to these smaller scale clients without incurring considerable transportation costs. Previously, individuals interested in reducing their waste stream or producing energy via AD were forced to pay to have their feedstocks shipped to larger facilities, reducing the financial benefit of engaging in this environmentally conscious process.

The System offers the ability to treat waste streams at a variety of scales with the added benefit of operating on site, thus eliminating the need for shipment to remote facilities. Furthermore, the modularity of the System makes it suitable for handling a variety of waste streams including animal manures and food wastes. One option for the System involves the removal of phosphorus and nitrogen, i.e., ammonia, from waste streams with high concentrations of these compounds. Importantly, this removal operates in-line with the greater AD process, thus avoiding the need for a separate nutrient recovery process, which is often required in other similar products. The fertilizer produced by the System is customizable in terms of phase, i.e., liquid vs. solid, as well as nutrient content by combining the cake (rich in trace elements important for crop growth) with nitrogen, phosphorus, and potassium rich byproducts in controllable proportions.

Figure 11:
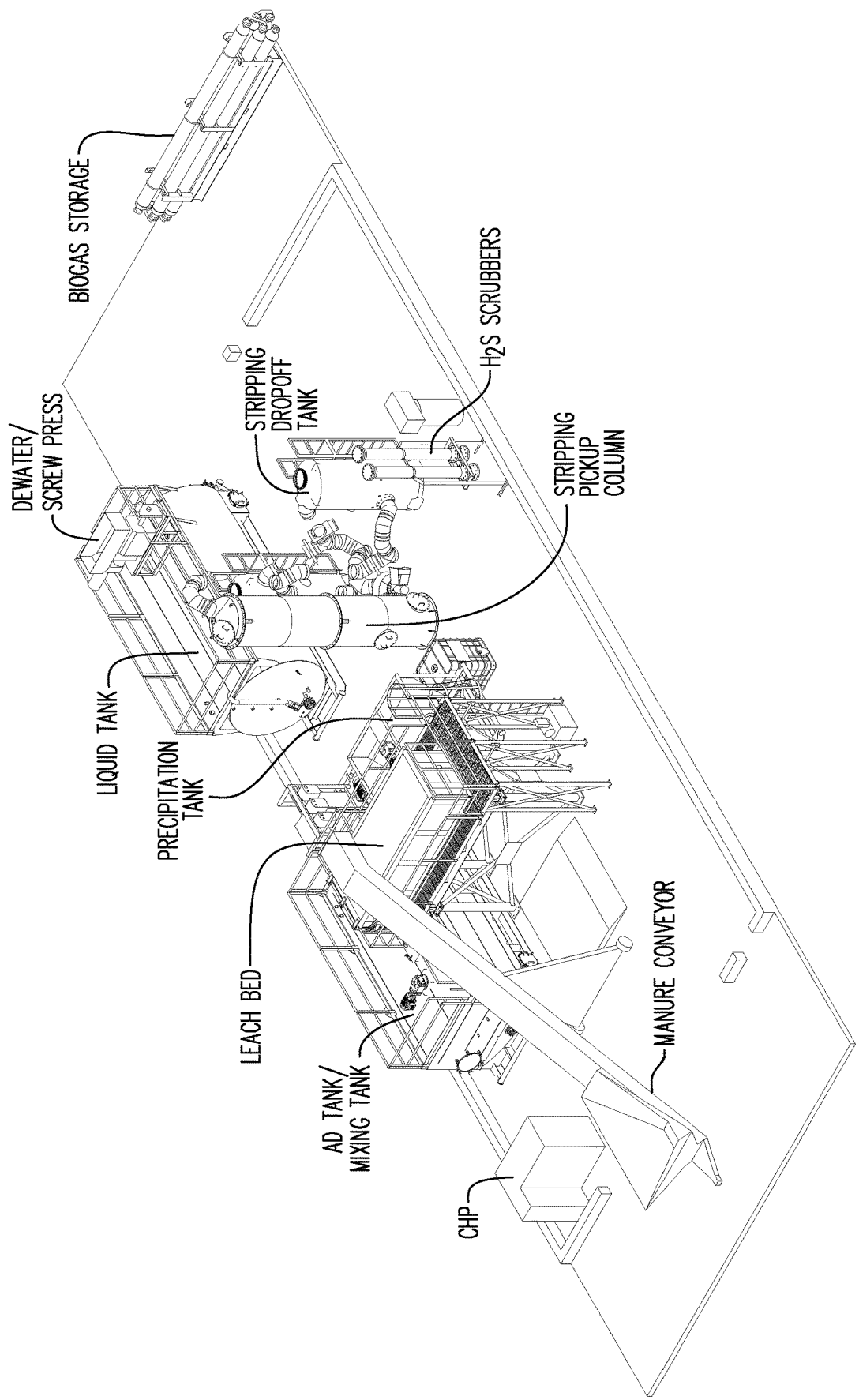
FIG. 11 is a plan view of a larger scale modular anaerobic digester system of the invention.

In order to handle greater volumes of organic material from a larger producer, additional AD tanks may be added to the System design or scaling up the size of the components, thereby increasing the overall capacity of the System. This leads to a corresponding increase in the size of all components as shown, for example, in FIG. 11. While the size is scaled up, the interaction between each component and the overall theory of the System remains the same. Similarly, these systems can also be downsized to serve as lab-scale Systems. Such reduced Systems are well suited for use in classrooms or single resident applications. Furthermore, due to the modularity of the System, it may be equipped with precipitation and stripping tanks or leach bed as needed, or, if footprint is a greater concern, can be produced without these components and still produce biogas for fueling natural gas engines. This allows for the ability to handle a variety of feedstocks. For example, if food waste is being processed in place of manure, a grinder pump may be equipped on the front end of the System to process the packaging, silverware, bones, etc. which are present in typical municipal food waste streams. If desirable, heat produced during this burning can be captured using a CHP engine. This heat can be subsequently used on site to heat buildings, water, etc. and further reduce reliance on fossil fuels. If no use is immediately available for the produced biogas, the System may be equipped with a flare to exhaust the produced gas.

The System operates under the well-established anaerobic digestion process, specifically taking advantage of methanogenesis: a process in which methanogenic bacteria convert carbon-based feedstocks into methane gas. Feedstocks containing organic material, e.g., sugars, proteins, fibers, lipids, are all available for conversion into methane under anaerobic conditions. Methanogens require specific parameters to be met to allow methanogenesis to proceed including (a) anoxic conditions, (b) mesophilic temperatures (95-100° F.), and (c) controlled pH of about 7.2. This explains the need to keep these conditions consistent during the AD process and the ability to process a variety of feedstocks.

AD proceeds most effectively when (a) the feedstock is prepared at an ideal percentage total solids content (feedstock specific), (b) liquid and solid phases often come in contact with each other, and (c) inhibitor concentration is kept minimal. To address the former requirement, the mixing tank allows for controlled addition of both solids and liquids from the liquids tank before homogenization of the feedstock prior to introduction into the AD tank. The second point is best addressed by the mixing line equipped within the AD reactor which transfers solids from the bottom of the reactor to the top of the feedstock, allowing them to drift through the liquid phase and settle once more after thoroughly mixing the two phases. This allows for phase combination using minimal energy, as the pump only needs to operate for a small period of time intermittently, rather than traditional methods which make use of a constantly cycling rotor. The third parameter is addressed by the leaching and stripping processes which each serve to remove some of the many inhibitors of anaerobic digestion, e.g., ammonia, potassium, and humic acids, from different feedstocks. Prior to introduction into the AD reactor, solids are treated for the removal of inhibitors during the leaching process. As most of these inhibitors are water-soluble, the extended contact between chemicals and the liquid phase during the passive leaching of water through the solids allows for dissolution to occur. As the leachate elutes from the leach bed, it is characterized as a highly concentrated solution of inhibitors, e.g., potassium, and other soluble solids, leaving behind solids which have been purified to a degree, facilitating their subsequent digestion.

Stripping proceeds when the pH of the feedstock slurry within the AD reactor reaches about 8. This is sufficiently basic to promote the volatilization of ammonia from solution. By passing the feedstock slurry over solid media, it is thinned to a degree which maximizes the exposed surface area. This likewise offers the most area available for ammonia (or other gases) to pass from the liquid phase to the gas phase, at which point it can be carried by the air flowing through the system into the stripping dropoff tank. The sulfuric acid within the dropoff tank reacts directly with ammonia to form aqueous ammonium sulfate (($NH_4$)$_2SO_4$). If hydrogen sulfide or carbon dioxide removal is desired, the dropoff tank can be filled with sodium hydroxide. The removal of ammonia from the feedstock slurry results in a decrease in pH back towards neutral, which is the preferred range for methanogens to operate. By repeating the stripping process multiple times, the overall ammonia content in the feedstock slurry can be considerably reduced.

The precipitation process operates via the formation of metal phosphate solids due to pH rise from the off gassing of $CO_2$ or the addition of base to leachate or feedstock slurry isolated from the AD tank. Within the leachate or feedstock slurry, phosphorus exists either as free phosphate or integrated into organic molecules or complexes. Upon the escape of $CO_2$ from solution or the addition of basic metals (e.g., $Ca(OH)_2$, $Mg(OH)_2$), a fraction of this phosphorus is able to form metal phosphate compounds, e.g., struvite, which are insoluble in water. Thus, they precipitate from solution and slowly settle to the bottom of the precipitation tank as a layer of solid which can be subsequently retrieved. This process is further facilitated by mixing and/or bubbling of air through the liquid being treated. By repeating the precipitation process multiple times, the overall phosphorus content in the feedstock can be considerably reduced.

Example

Prior to starting the System with a batch of organic waste material, liquid in the liquids tank should be warmed to about 100° F. by turning the electric blanket on. Initially, the organic waste, e.g., manure, food waste, crop waste, etc., will be weighed and added to the mixing tank. If chicken manure is being used, it should first be added to the leaching bed and leached with water to remove inhibitors. After addition to the mixing tank, liquid from the liquids tank, e.g., heated water, slurry, liquor, should be added to the waste to create a feedstock slurry of appropriate percentage total solids (% TS) based on the volume of liquid passed through the water totalizer. This value is determined experimentally and varies based on feedstock to maximize efficiency of the anaerobic digestion process. After dilution, the feedstock solids and the liquids should be mixed using a mixer or other mechanical blending apparatus. Once the feedstock slurry is prepared, the mixing tank is attached to piping and the feedstock slurry is passed through the maceration pump to the AD reactor. If necessary, this process is repeated until the AD reactor is filled with feedstock slurry while leaving about 10% of its volume empty as headspace. At this point, the mixing tank is detached from the System and the AD reactor is sealed, i.e., top closed, to initiate the batch. The AD reactor should be mixed using the mixing pump at least once daily for about 15-30 seconds. While the batch proceeds, pH of the liquids should be monitored to serve as a general measure of methanogen health. If the pH drops low, i.e., significantly below 6.8 or so, the batch should be treated to raise the pH back to neutral. This treatment can include carbon dioxide stripping or the addition of basic chemicals. Other liquid parameters, e.g., nutrient content, buffering capacity, etc., can be measured by taking samples of slurry daily after mixing. Similarly, biogas production and methane content should be monitored closely over the first about 3-5 days of batch operation. During this time, biogas production should initiate, though the extent of which will vary depending on feedstock and microbial adaptation. In general, it can be expected that the biogas produced in this early phase of digestion will be fairly rich in carbon dioxide as hydrolysis proceeds. Importantly, this biogas will be passively treated by the scrubbing system to remove hydrogen sulfide and water from the mixture. This treated biogas will be stored in the gas bladder where it can be used as needed to operate traditional generators and engines. By the end of the first week, methane should begin to evolve and continue to compose a greater portion of the biogas as the batch proceeds. From this point on, methane production can be used as a measure of methanogen health, which should be maximized to yield the highest quality biogas possible. If nutrient sequestration is required, liquid transfer pumps can be used to transport feedstock slurry to the precipitation tank where $CO_2$ can be bubbled through the tank or basic chemicals can be added to drive the precipitation of phosphorus. Eventually, whether through artificial, i.e., $CO_2$ stripping or chemical addition, or normal, i.e., anaerobic digestion, means, the pH of the slurry will reach about 8. At this point, the liquid transfer pumps in the system should be utilized to shunt slurry from the AD reactor or precipitation tank through the stripping pickup column with the fan 105 operating. The air from the fan 105 will carry the ammonia which is released from the feedstock slurry into the stripping dropoff tank, which is pre-coated with acid. Continue this process until the holding tank of the stripping column is filled with feedstock slurry, then transfer it back to the main AD reactor. If the pH of the feedstock slurry in the AD reactor is still high, repeat this stripping process until it is brought back to neutral. After stripping, measure the pH of the acid within the dropoff tank to ensure that it is still acidic. If neutral, refresh the acid. These precipitation and stripping processes can be repeated as needed during the batch to maintain the health of the microbial population. A typical retention time is approximately 21 days, however this can be extended as needed, though biogas production will generally diminish over longer timespans. Once the batch is concluded, the mixing pump can be used to shuttle feedstock slurry to the discharge port. This port can be equipped with a hose or piping to direct the feedstock slurry to the proper place at this point whether it be direct application to a field or dewatering in a screw press or other apparatus. Once the tank is emptied, it is immediately ready to load with the subsequent batch of organic waste following the same procedure outlined here.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. A modular anaerobic digestion point-of-waste to renewable energy system for converting an organic feedstock material into a biogas and a digestate which digestate is separated into solid and liquid components by dewatering ("System") comprising
    a leaching bed adapted to receive the organic feedstock material and water to remove inhibitory nutrients;
    a mixing tank adapted to receive from the leaching bed a leached feedstock;
    a liquids tank adapted to provide liquids to the mixing tank;
    a means for macerating the leached feedstock and the liquids in the mixing tank into a feedstock slurry;
    an anaerobic digester reactor wherein the feedstock slurry is pumped from the mixing tank into the anaerobic digester reactor and wherein anaerobic digestion takes place to convert the feedstock slurry into the biogas and the digestate;
    a precipitation tank and a stripping tank wherein a portion of the feedstock slurry in the anaerobic digestion reactor is pumped first into the precipitation tank and then into the stripping tank, the precipitation tank and the stripping tank adapted to clean the feedstock slurry of at least ammonia and phosphorus, wherein the cleaned feedstock slurry is pumped back into the anaerobic digester reactor;
    a hydrogen sulfide scrubber adapted to receive the biogas wherein the hydrogen sulfide scrubber removes hydrogen sulfide from the biogas;
    a water remover tank adapted to receive the biogas wherein water is removed from the biogas;
    a gas bladder adapted to receive the biogas from the hydrogen sulfide scrubber wherein the biogas is stored for subsequent use;
    a dewaterer adapted to receive the digestate from the anaerobic digester reactor wherein the digestate is dewatered for subsequent use; and
    wherein the system is adapted to be located at the point-of-waste and is adapted to be scaled to handle the volume of organic material by alternating the size or number of the components thereof.

2. The system of claim 1 wherein the mixing tank includes a rotary mixer and a macerator pump.

3. The system of claim 1 wherein the liquids tank includes a means for heating the liquids.

4. The system of claim 1 wherein the stripping tank includes a stripping pickup column and a stripping dropoff tank.

5. The system of claim 1 wherein the hydrogen sulfide scrubber comprises two scrubbing tanks where a first scrubbing tank includes an iron sponge and a second scrubbing tank includes activated charcoal and wherein the biogas is first treated in the first scrubbing tank and then transferred to the water remover tank and the biogas is then transferred to the second scrubbing tank.

6. The system of claim 1 wherein the mixing tank includes a rotary mixer and a macerator pump, the liquids tank includes a means for heating the liquids, the stripping tank includes a stripping pickup column and a stripping dropoff tank and the hydrogen sulfide scrubber comprises two scrubbing tanks where a first scrubbing tank includes an iron sponge and a second scrubbing tank includes activated charcoal and wherein the biogas is first treated in the first scrubbing tank and transferred to the water remover and the biogas is then transferred to the second scrubbing tank.

7. A method of treating an organic feedstock by anaerobic digestion at a point-of-waste location to convert the organic feedstock into a biogas and a digestate comprising the steps of
  a. providing the organic feedstock to a modular system comprising
   a leaching bed adapted to receive the organic feedstock material and water to remove inhibitory nutrients;
   a mixing tank adapted to receive from the leaching bed a leached feedstock;
   a liquids tank adapted to provide liquids to the mixing tank;
   a means for macerating the leached feedstock and the liquids in the mixing tank into a feedstock slurry;
   an anaerobic digester reactor wherein the feedstock slurry is pumped from the mixing tank into the anaerobic digester reactor and wherein anaerobic digestion takes place to convert the feedstock slurry into the biogas and the digestate;
   a precipitation tank and a stripping tank wherein a portion of the feedstock slurry in the anaerobic digestion reactor is pumped first into the precipitation tank and then into the stripping tank, the precipitation tank and the stripping tank adapted to clean the feedstock slurry of at least ammonia and phosphorus, wherein the cleaned feedstock slurry is pumped back into the anaerobic digester reactor;
   a hydrogen sulfide scrubber adapted to receive the biogas wherein the hydrogen sulfide scrubber removes hydrogen sulfide from the biogas;
   a water remover tank adapted to receive the biogas wherein water is removed from the biogas;
   a gas bladder adapted to receive the biogas from the hydrogen sulfide scrubber wherein the biogas is stored for subsequent use;
   a dewaterer adapted to receive the digestate from the anaerobic digester reactor wherein the digestate is dewatered for subsequent use; and
   wherein the system is adapted to be located at the point-of-waste and is adapted to be scaled to handle the volume of organic material by alternating the size or number of the components thereof;
  b. treating the organic feedstock in the modular system; and
  c. obtaining a biogas and a digestate providing a source of renewable energy.

8. The method of claim 7 wherein the mixing tank includes a rotary mixer and a macerator pump.

9. The method of claim 7 wherein the liquids tank includes a means for heating the liquids.

10. The method of claim 7 wherein the stripping tank includes a stripping pickup column and a stripping dropoff tank.

11. The method of claim 7 wherein the hydrogen sulfide scrubber comprises two scrubbing tanks where a first scrubbing tank includes an iron sponge and a second scrubbing tank includes activated charcoal and wherein the biogas is first treated in the first scrubbing tank and then transferred to the water remover tank and the biogas is then transferred to the second scrubbing tank.

12. The method of claim 7 wherein the mixing tank includes a rotary mixer and a macerator pump, the liquids tank includes a means for heating the liquids, the stripping tank includes a stripping pickup column and a stripping dropoff tank and the hydrogen sulfide scrubber comprises two scrubbing tanks where a first scrubbing tank includes an iron sponge and a second scrubbing tank includes activated charcoal and wherein the biogas is first treated in the first scrubbing tank and transferred to the water remover and the biogas is then transferred to the second scrubbing tank.

* * * * *